US008506558B2

(12) United States Patent
Gertner et al.

(10) Patent No.: US 8,506,558 B2
(45) Date of Patent: *Aug. 13, 2013

(54) SYSTEM AND METHOD FOR PERFORMING AN OCULAR IRRADIATION PROCEDURE

(75) Inventors: Michael Gertner, Menlo Park, CA (US); Mark Arnoldussen, San Carlos, CA (US); Matt Herron, Palo Alto, CA (US)

(73) Assignee: Oraya Therapeutics, Inc., Newark, CA (US)

( * ) Notice: Subject to any disclaimer, the term of this patent is extended or adjusted under 35 U.S.C. 154(b) by 1387 days.

This patent is subject to a terminal disclaimer.

(21) Appl. No.: 12/027,069

(22) Filed: Feb. 6, 2008

(65) Prior Publication Data

US 2009/0182310 A1 Jul. 16, 2009

Related U.S. Application Data

(60) Provisional application No. 61/020,655, filed on Jan. 11, 2008.

(51) Int. Cl.
*A61F 9/007* (2006.01)
*A61B 18/18* (2006.01)
*A61N 5/01* (2006.01)

(52) U.S. Cl.
USPC .................................. 606/4; 606/12; 378/65

(58) Field of Classification Search
None
See application file for complete search history.

(56) References Cited

U.S. PATENT DOCUMENTS

| | | |
|---|---|---|
| 3,073,960 A | 1/1963 | Guentner et al. |
| 4,391,275 A | 7/1983 | Fankhauser et al. |
| 4,521,905 A | 6/1985 | Hosokawa |
| 4,710,193 A | 12/1987 | Volk |
| 4,718,418 A | 1/1988 | L'Esperance, Jr. |
| 4,817,432 A | 4/1989 | Wallace et al. |
| 5,008,907 A | 4/1991 | Norman et al. |
| 5,027,818 A | 7/1991 | Bova et al. |
| 5,065,031 A | 11/1991 | Moscovitch |
| 5,116,115 A | 5/1992 | Lange et al. |
| 5,139,494 A | 8/1992 | Freiberg |
| 5,171,254 A | 12/1992 | Sher |
| 5,189,687 A | 2/1993 | Bova et al. |
| 5,207,223 A | 5/1993 | Adler |
| 5,216,255 A | 6/1993 | Weidlich |
| 5,304,167 A | 4/1994 | Freiberg |
| 5,336,215 A * | 8/1994 | Hsueh et al. ................... 606/4 |
| 5,339,347 A | 8/1994 | Slatkin et al. |
| 5,354,323 A | 10/1994 | Whitebook |
| 5,373,844 A | 12/1994 | Smith et al. |
| 5,411,026 A | 5/1995 | Carol |
| 5,422,926 A | 6/1995 | Smith et al. |
| 5,427,097 A | 6/1995 | Depp |
| 5,430,308 A | 7/1995 | Feichtner et al. |
| 5,446,548 A | 8/1995 | Gerig et al. |
| 5,468,238 A | 11/1995 | Mersch |
| 5,528,652 A | 6/1996 | Smith et al. |
| 5,556,417 A | 9/1996 | Sher |
| 5,635,721 A | 6/1997 | Bardi et al. |
| 5,644,616 A | 7/1997 | Landi et al. |
| 5,651,043 A | 7/1997 | Tsuyuki et al. |
| 5,668,847 A | 9/1997 | Hernandez |
| 5,708,696 A | 1/1998 | Kantor |
| 5,724,400 A | 3/1998 | Swerdloff et al. |
| 5,727,042 A | 3/1998 | Brenneisen |
| 5,737,384 A | 4/1998 | Fenn |
| 5,744,919 A | 4/1998 | Mishin et al. |
| 5,745,545 A | 4/1998 | Hughes |
| 5,771,270 A | 6/1998 | Archer |
| 5,778,043 A | 7/1998 | Cosman |
| 5,820,553 A | 10/1998 | Hughes |
| 5,870,697 A | 2/1999 | Chandler et al. |
| 5,901,199 A | 5/1999 | Murphy et al. |
| 6,001,054 A | 12/1999 | Regulla et al. |
| 6,104,778 A | 8/2000 | Murad |
| 6,126,668 A | 10/2000 | Bair et al. |
| 6,134,294 A * | 10/2000 | Gibbs .............................. 378/65 |

(Continued)

FOREIGN PATENT DOCUMENTS

| | | |
|---|---|---|
| EP | 2152145 A1 | 2/2010 |
| EP | 2231277 A1 | 9/2010 |

(Continued)

OTHER PUBLICATIONS

International Search Report and Written Opinion for PCT/US2008/012341, search report dated Feb. 5, 2009, 21 pages (2009).
Cornsweet, T.N. and Crane, H.D., "Accurate Two-Dimensional Eye Tracker Using First and Fourth Purkinje", *Journal of the Optical Society of America*, 63(8):921-928 (1973).
Das et al., "Small Fields: Nonequilibrium Radiation Dosimetry", *Medical Physics*, 35(1):206-215 (2008).
Esquivel, Carlos Jr. et al., Novel low-kVp beamlet system for choroidal melanoma, *Radiation Oncology*, I:36, 12 pages (2006).
Fakiris, Achilles J. et al., Gamma-Knife-Based Stereotactic Radiosurgery for Uveal Melanoma, *Stereotactic and Functional. Neurosurgery.*, 85:106-112 (2007).

(Continued)

*Primary Examiner* — Robert A. Wax
*Assistant Examiner* — H. Sarah Park
(74) *Attorney, Agent, or Firm* — James W. Hill; M. Todd Hales; McDermott Will & Emery LLP

(57) ABSTRACT

A method and system for performing an ocular irradiation procedure on a patient's eye is disclosed. The system includes a head support for supporting the patient's head, an eye-contact device attachable to the front portion of the patient's eye, to stabilize the position of the eye; and a position detector for determining the position of the contact device in the external coordinate system. A source of a collimated electromagnetic radiation beam in the system is controlled by a beam-positioning assembly for positioning the beam source such that the beam, when activated, is aimed along a selected path at a selected coordinate in the external coordinate system corresponding to a selected target region in the patient's eye.

14 Claims, 17 Drawing Sheets

(56) References Cited

U.S. PATENT DOCUMENTS

| | | |
|---|---|---|
| 6,135,996 A | 10/2000 | Kolesa et al. |
| 6,144,875 A | 11/2000 | Schweikard et al. |
| 6,149,643 A | 11/2000 | Herekar et al. |
| 6,179,422 B1 | 1/2001 | Lai |
| 6,245,059 B1 | 6/2001 | Clapham |
| 6,257,722 B1 | 7/2001 | Toh |
| 6,260,005 B1 | 7/2001 | Yang et al. |
| 6,278,764 B1 | 8/2001 | Barbee, Jr. et al. |
| 6,287,299 B1 | 9/2001 | Sasnett et al. |
| 6,299,054 B1 | 10/2001 | Gibbs, Jr. |
| 6,299,307 B1 | 10/2001 | Oltean et al. |
| 6,301,328 B1 | 10/2001 | Sliski et al. |
| 6,301,329 B1 | 10/2001 | Surridge |
| 6,312,393 B1 | 11/2001 | Abreu |
| 6,359,963 B1 | 3/2002 | Cash |
| 6,373,571 B1 | 4/2002 | Juhasz et al. |
| 6,385,286 B1 | 5/2002 | Fitchard et al. |
| 6,405,072 B1 | 6/2002 | Cosman |
| 6,436,113 B1 | 8/2002 | Burba et al. |
| 6,459,762 B1 | 10/2002 | Wong et al. |
| 6,494,878 B1 | 12/2002 | Pawlowski et al. |
| 6,501,981 B1 | 12/2002 | Schweikard et al. |
| 6,512,813 B1 | 1/2003 | Krispel et al. |
| 6,535,574 B1 | 3/2003 | Collins et al. |
| 6,544,193 B2 | 4/2003 | Abreu |
| 6,560,312 B2 | 5/2003 | Cash |
| 6,621,889 B1 | 9/2003 | Mostafavi |
| 6,690,965 B1 | 2/2004 | Riaziat et al. |
| 6,714,620 B2 | 3/2004 | Caflisch et al. |
| 6,728,335 B1 | 4/2004 | Thomson et al. |
| 6,744,846 B2 | 6/2004 | Popescu et al. |
| 6,778,850 B1 | 8/2004 | Adler et al. |
| 6,789,900 B2 | 9/2004 | Van de Velde |
| 6,792,073 B2 | 9/2004 | Deasy et al. |
| 6,810,107 B2 | 10/2004 | Steinberg |
| 6,837,862 B2 | 1/2005 | Driver, Jr. |
| 6,853,704 B2 | 2/2005 | Collins et al. |
| 6,863,667 B2 | 3/2005 | Webb et al. |
| 6,865,253 B2 | 3/2005 | Blumhofer et al. |
| 6,865,254 B2 | 3/2005 | Nafstadius |
| 6,875,165 B2 | 4/2005 | Dejuan, Jr. et al. |
| 6,888,919 B2 | 5/2005 | Graf et al. |
| 6,937,696 B1 | 8/2005 | Mostafavi |
| 6,942,656 B2 | 9/2005 | Pawlowski et al. |
| 6,965,847 B2 | 11/2005 | Wessol et al. |
| 6,977,987 B2 | 12/2005 | Yamashita et al. |
| 6,990,175 B2 | 1/2006 | Nakashima et al. |
| 7,018,376 B2 | 3/2006 | Webb et al. |
| 7,027,557 B2 | 4/2006 | Llacer |
| 7,044,602 B2 | 5/2006 | Chernyak |
| 7,046,762 B2 | 5/2006 | Lee |
| 7,046,765 B2 | 5/2006 | Wong et al. |
| 7,070,327 B2 | 7/2006 | Collins |
| 7,070,554 B2 | 7/2006 | White et al. |
| 7,085,347 B2 | 8/2006 | Mihara et al. |
| 7,103,144 B2 | 9/2006 | Wong et al. |
| 7,103,145 B2 | 9/2006 | Wong et al. |
| 7,115,120 B2 | 10/2006 | Lin |
| 7,139,601 B2 | 11/2006 | Bucholz et al. |
| 7,154,991 B2 | 12/2006 | Earnst et al. |
| 7,158,607 B2 | 1/2007 | Dimanian et al. |
| 7,158,610 B2 | 1/2007 | Mostafavi |
| 7,166,852 B2 | 1/2007 | Saracen et al. |
| 7,171,257 B2 | 1/2007 | Thomson |
| 7,178,666 B2 | 2/2007 | Huang |
| 7,179,254 B2 | 2/2007 | Pendekanti et al. |
| 7,187,792 B2 | 3/2007 | Fu et al. |
| 7,194,063 B2 | 3/2007 | Dilmanian et al. |
| 7,204,640 B2 | 4/2007 | Fu et al. |
| 7,221,733 B1 | 5/2007 | Takai et al. |
| 7,225,012 B1 | 5/2007 | Susil et al. |
| 7,227,925 B1 | 6/2007 | Mansfield et al. |
| 7,231,076 B2 | 6/2007 | Fu et al. |
| 7,239,684 B2 | 7/2007 | Hara et al. |
| 7,239,908 B1 | 7/2007 | Alexander et al. |
| 7,260,426 B2 | 8/2007 | Schweikard et al. |
| 7,266,176 B2 | 9/2007 | Allison et al. |
| 7,278,787 B2 | 10/2007 | Hack et al. |
| 7,280,865 B2 | 10/2007 | Adler et al. |
| 7,283,610 B2 | 10/2007 | Low et al. |
| 7,346,144 B2 | 3/2008 | Hughes et al. |
| 7,418,079 B2 | 8/2008 | Schildkraut et al. |
| 7,453,983 B2 | 11/2008 | Schildkraut et al. |
| 7,453,984 B2 | 11/2008 | Chen et al. |
| 7,496,174 B2 | 2/2009 | Gertner et al. |
| 7,505,559 B2 | 3/2009 | Kuduvalli |
| 7,535,991 B2 | 5/2009 | Gertner |
| 7,564,946 B2 | 7/2009 | Gertner |
| 7,587,024 B2 | 9/2009 | Grozinger et al. |
| 7,590,219 B2 | 9/2009 | Maurer et al. |
| 7,620,144 B2 | 11/2009 | Bodduluri |
| 7,620,147 B2 | 11/2009 | Gertner et al. |
| 7,672,429 B2 | 3/2010 | Urano et al. |
| 7,680,244 B2 | 3/2010 | Gertner et al. |
| 7,680,245 B2 | 3/2010 | Gertner et al. |
| 7,693,258 B2 | 4/2010 | Gertner |
| 7,693,259 B2 | 4/2010 | Gertner |
| 7,693,260 B2 | 4/2010 | Gertner et al. |
| 7,697,663 B2 | 4/2010 | Gertner |
| 7,792,249 B2 | 9/2010 | Gertner et al. |
| 7,801,271 B2 | 9/2010 | Gertner et al. |
| 7,822,175 B2 | 10/2010 | Gertner |
| 7,831,073 B2 | 11/2010 | Fu et al. |
| 7,894,649 B2 | 2/2011 | Fu et al. |
| 7,912,178 B2 | 3/2011 | Gertner |
| 7,912,179 B2 | 3/2011 | Gertner et al. |
| 7,953,203 B2 | 5/2011 | Gertner et al. |
| 7,961,845 B2 | 6/2011 | Gertner et al. |
| 7,978,818 B2 | 7/2011 | Gertner et al. |
| 7,978,819 B2 | 7/2011 | Gertner et al. |
| 2002/0051513 A1 | 5/2002 | Pugachev et al. |
| 2002/0065461 A1 | 5/2002 | Cosman |
| 2002/0099363 A1 | 7/2002 | Woodward et al. |
| 2002/0106054 A1 | 8/2002 | Caflisch et al. |
| 2002/0106055 A1 | 8/2002 | Cash |
| 2002/0115902 A1 | 8/2002 | Dejuan et al. |
| 2002/0131556 A1 | 9/2002 | Steinberg |
| 2002/0161356 A1 | 10/2002 | Bille et al. |
| 2002/0198453 A1 | 12/2002 | Herrick, II |
| 2002/0198553 A1 | 12/2002 | Schumer et al. |
| 2003/0112922 A1 | 6/2003 | Burdette et al. |
| 2003/0120141 A1 | 6/2003 | Adler |
| 2003/0125622 A1 | 7/2003 | Schweikard et al. |
| 2003/0161826 A1 | 8/2003 | Arnason et al. |
| 2003/0189689 A1 | 10/2003 | Rathjen |
| 2003/0211075 A1 | 11/2003 | Thorpe et al. |
| 2003/0219098 A1 | 11/2003 | McNutt et al. |
| 2004/0019274 A1 | 1/2004 | Galloway, Jr. et al. |
| 2004/0037390 A1 | 2/2004 | Mihara et al. |
| 2004/0054359 A1 | 3/2004 | Ruiz et al. |
| 2004/0071261 A1 | 4/2004 | Earl et al. |
| 2004/0131150 A1 | 7/2004 | Pankratov et al. |
| 2004/0138515 A1 | 7/2004 | White et al. |
| 2004/0267294 A1 | 12/2004 | Will |
| 2005/0010109 A1 | 1/2005 | Faul |
| 2005/0049478 A1 | 3/2005 | Kuduvalli et al. |
| 2005/0058245 A1 | 3/2005 | Ein-Gal |
| 2005/0111621 A1 | 5/2005 | Riker et al. |
| 2005/0175218 A1 | 8/2005 | Vertegaal et al. |
| 2005/0180544 A1 | 8/2005 | Sauer et al. |
| 2005/0192562 A1 | 9/2005 | Loesel et al. |
| 2005/0203499 A1 | 9/2005 | Pendekanti et al. |
| 2005/0226482 A1 | 10/2005 | Kuduvalli |
| 2005/0228255 A1 | 10/2005 | Saracen et al. |
| 2005/0234327 A1 | 10/2005 | Saracen et al. |
| 2005/0270486 A1 | 12/2005 | Teiwes et al. |
| 2005/0271590 A1 | 12/2005 | Schwartz et al. |
| 2006/0002601 A1 | 1/2006 | Fu et al. |
| 2006/0002615 A1 | 1/2006 | Fu et al. |
| 2006/0002630 A1 | 1/2006 | Fu et al. |
| 2006/0002631 A1 | 1/2006 | Fu et al. |
| 2006/0002632 A1 | 1/2006 | Fu et al. |
| 2006/0004281 A1 | 1/2006 | Saracen |
| 2006/0033044 A1 | 2/2006 | Gentry et al. |

| | | | |
|---|---|---|---|
| 2006/0067469 A1 | 3/2006 | Dooley et al. | |
| 2006/0072821 A1 | 4/2006 | Wang | |
| 2006/0074292 A1 | 4/2006 | Thomson et al. | |
| 2006/0074299 A1 | 4/2006 | Sayeh | |
| 2006/0074304 A1 | 4/2006 | Sayeh | |
| 2006/0078087 A1 | 4/2006 | Forman et al. | |
| 2006/0084952 A1 | 4/2006 | Pallikaris et al. | |
| 2006/0093089 A1 | 5/2006 | Vertatschitsch et al. | |
| 2006/0170679 A1 | 8/2006 | Wang et al. | |
| 2006/0170865 A1 | 8/2006 | Hirohara et al. | |
| 2006/0176997 A1 | 8/2006 | Dilmanian et al. | |
| 2006/0182326 A1 | 8/2006 | Schildkraut et al. | |
| 2006/0192921 A1* | 8/2006 | Loesel et al. | 351/219 |
| 2006/0193441 A1 | 8/2006 | Cadman | |
| 2006/0199991 A1 | 9/2006 | Lewis et al. | |
| 2006/0203964 A1 | 9/2006 | Nyholm et al. | |
| 2006/0245543 A1 | 11/2006 | Earnst et al. | |
| 2006/0271025 A1* | 11/2006 | Jones et al. | 606/4 |
| 2006/0274061 A1 | 12/2006 | Wang et al. | |
| 2006/0274885 A1 | 12/2006 | Wang et al. | |
| 2006/0274924 A1 | 12/2006 | West et al. | |
| 2006/0274925 A1 | 12/2006 | West et al. | |
| 2006/0285641 A1 | 12/2006 | Scherch | |
| 2006/0287662 A1 | 12/2006 | Berry et al. | |
| 2006/0291621 A1 | 12/2006 | Yan et al. | |
| 2006/0291710 A1 | 12/2006 | Wang et al. | |
| 2006/0293583 A1 | 12/2006 | Saracen et al. | |
| 2007/0003007 A1 | 1/2007 | Carrano et al. | |
| 2007/0003123 A1 | 1/2007 | Fu et al. | |
| 2007/0015991 A1 | 1/2007 | Fu et al. | |
| 2007/0038058 A1 | 2/2007 | West et al. | |
| 2007/0053490 A1 | 3/2007 | Wang et al. | |
| 2007/0053491 A1 | 3/2007 | Schildkraut et al. | |
| 2007/0071168 A1 | 3/2007 | Allison et al. | |
| 2007/0071176 A1 | 3/2007 | Main et al. | |
| 2007/0078306 A1 | 4/2007 | Allison et al. | |
| 2007/0083087 A1 | 4/2007 | Carda | |
| 2007/0093795 A1 | 4/2007 | Melcher et al. | |
| 2007/0118010 A1 | 5/2007 | Hillstead et al. | |
| 2007/0127622 A1 | 6/2007 | Main et al. | |
| 2007/0127845 A1 | 6/2007 | Fu et al. | |
| 2007/0140413 A1 | 6/2007 | Saracen | |
| 2007/0169265 A1 | 7/2007 | Saracen et al. | |
| 2007/0195929 A1 | 8/2007 | Ruchala et al. | |
| 2007/0225691 A1 | 9/2007 | Silvestrini et al. | |
| 2007/0225693 A1 | 9/2007 | Muehlhoff et al. | |
| 2007/0249911 A1 | 10/2007 | Simon | |
| 2008/0049896 A1 | 2/2008 | Kuduvalli | |
| 2008/0056434 A1 | 3/2008 | Grozinger et al. | |
| 2008/0159478 A1 | 7/2008 | Keall et al. | |
| 2008/0187099 A1 | 8/2008 | Gertner | |
| 2008/0187101 A1 | 8/2008 | Gertner | |
| 2008/0192892 A1 | 8/2008 | Dilmanian et al. | |
| 2008/0212737 A1 | 9/2008 | D'Souza et al. | |
| 2008/0212738 A1 | 9/2008 | Gertner | |
| 2008/0317312 A1 | 12/2008 | Carl et al. | |
| 2009/0003525 A1 | 1/2009 | Gertner et al. | |
| 2009/0163898 A1 | 6/2009 | Gertner et al. | |
| 2009/0182310 A1 | 7/2009 | Gertner et al. | |

FOREIGN PATENT DOCUMENTS

| | | |
|---|---|---|
| JP | 06-181945 A | 7/1994 |
| JP | 06-277248 A | 10/1994 |
| JP | 2000-509291 A | 7/2000 |
| JP | 2001-079102 A | 3/2001 |
| JP | 2002-502647 A | 1/2002 |
| JP | 2002-540837 A | 12/2002 |
| JP | 2004-501730 A | 1/2004 |
| JP | 2005-237730 A | 9/2005 |
| JP | 2007-501057 A | 1/2007 |
| JP | 2007-509668 A | 4/2007 |
| JP | 4043028 B2 | 2/2008 |
| JP | 4354737 B2 | 10/2009 |
| JP | 4436139 B2 | 1/2010 |
| JP | 4602356 B2 | 10/2010 |
| JP | 5086523 B2 | 11/2012 |
| WO | 9527453 A1 | 10/1995 |
| WO | 00/59395 A1 | 10/2000 |
| WO | WO-0126591 A1 | 4/2001 |
| WO | WO-0235996 A1 | 5/2002 |
| WO | 03/008543 A | 1/2003 |
| WO | WO-03/039370 A1 | 5/2003 |
| WO | 2005/016258 A2 | 2/2005 |
| WO | 2005/049139 A1 | 6/2005 |
| WO | 2005/079294 A2 | 9/2005 |
| WO | 2006/090217 A1 | 8/2006 |
| WO | WO-2006086631 A2 | 8/2006 |
| WO | WO-2007/027164 | 3/2007 |
| WO | 2007/045075 A1 | 4/2007 |
| WO | 2008/124801 A2 | 10/2008 |
| WO | 2008/150330 A1 | 12/2008 |
| WO | 2009/075714 A1 | 6/2009 |

OTHER PUBLICATIONS

Francescon et al., "Total Scatter Factors of Small Beans: A Multidetector and Monte Carlo Study", *Medical Physics*, 35(2):504-513 (2008).

Georgopoulos, Michael et al., Tumour Regression of Uveal Melanoma after Ruthenium-106 Brachytherapy or Stereotactic Radiotherapy with Gamma Knife or Linear Accelerator, *Ophthalmologica*, 217:315-319 (2003).

Kirwan, James F. et al., Effect of β radiation on success of glaucoma drainage surgery in South Africa: randomized controlled trial, *BMJ online*, BMJ doi:10.1136/bmj.38971.395301.7C (Oct. 5, 2006).

Kishi, Kazuhi et al., Lead Contact Lens for Crystalline Lens Shielding in Electron Therapy for Eyelid Tumors, *Radiation Medicine*, 14(2):107-109 (1996).

International Search Report and Written Opinion for PCT/US2008/013886, search report dated May 22, 2009, 19 pages (2009).

U.S. application and Preliminary Amendment U.S. Appl. No. 12/027,083, filed Feb. 6, 2008, 105 pages (2008).

U.S. application and Preliminary Amendment U.S. Appl. No. 12/027,094, filed Feb. 6, 2008, 111 pages (2008).

U.S. Appl. No. 12/103,534, filed Apr. 15, 2008, 99 pages (2008).

U.S. application and Preliminary Amendment U.S. Appl. No. 12/262,031, filed Oct. 30, 2008, 163 pages (2008).

U.S. Appl. No. 12/338,634, filed Dec. 18, 2008, 244 pages (2008).

Bogner, J. et al. 2003. A Noninvasive Eye Fixation and Computer-Aided Eye Monitoring System for Linear Accelerator-Based Stereotactic Radiotherapy of Uveal Melanoma. International Journal of Radiation Oncology Biology Physics, vol. 56, No. 4, Jun. 20, 2001, pp. 1128-1136.

Petersch, B. et al. 2004. Automatic Real-Time Surveillance of Eye Position and Gating for Stereotactic Radiotherapy of Uveal Melanoma. Medical Physics, vol. 31, No. 12, Nov. 24, 2004, pp. 3521-3527.

Extended European Search Report, dated Jun. 1, 2011, for European Patent Application No. 08743035.1, which entered the European Regional Phase on Dec. 3, 2009, Applicant Oraya Therapeutics, entitled "Device and Assembly for Positioning, Stabilizing and Treating an Eye," based on PCT Application No. PCT/US2008/004999.

International Search Report and Written Opinion for PCT/US2008/004999, search report dated Sep. 2, 2008, 9 pages (2008).

International Search Report and Written Opinion for PCT/US2008/005101, search report dated Sep. 2, 2008, 11 pages (2008).

Jaywant, S.E. et al., "Stereotactic Radiotherapy in the Treatment if Ocular Melanoma: A Noninvasive Eye Fixation Aid and Tracking System", *Journal of Applied Clinical Medical Physics*, 4(2):156-161 (2003).

Dieckmann et al., "A Linac-Based Stereotactic Irradiation Technique of Uveal Melanoma," Radiotherapy and Oncology, 61:49-56 (2001).

Gao et al., "Orthovoltage radiation therapy treatment planning using Monte Carlo Simulation: treatment of neuroendocrine carcinoma of the maxillary sinus," ISSN: 0031-9155; vol. 42, No. 12., pp. 2421-2433 (1997).

Kim et al., "Combination hyperthermia and radiation therapy for malignant melanoma," Cancer, 50:478-482 (1982).

Kobayashi et al., Radiotherapy for subfoveal neovascularisation associated with pathological myopia: a pilot study., J. Ophth. 87:761-766 (2000).

* cited by examiner

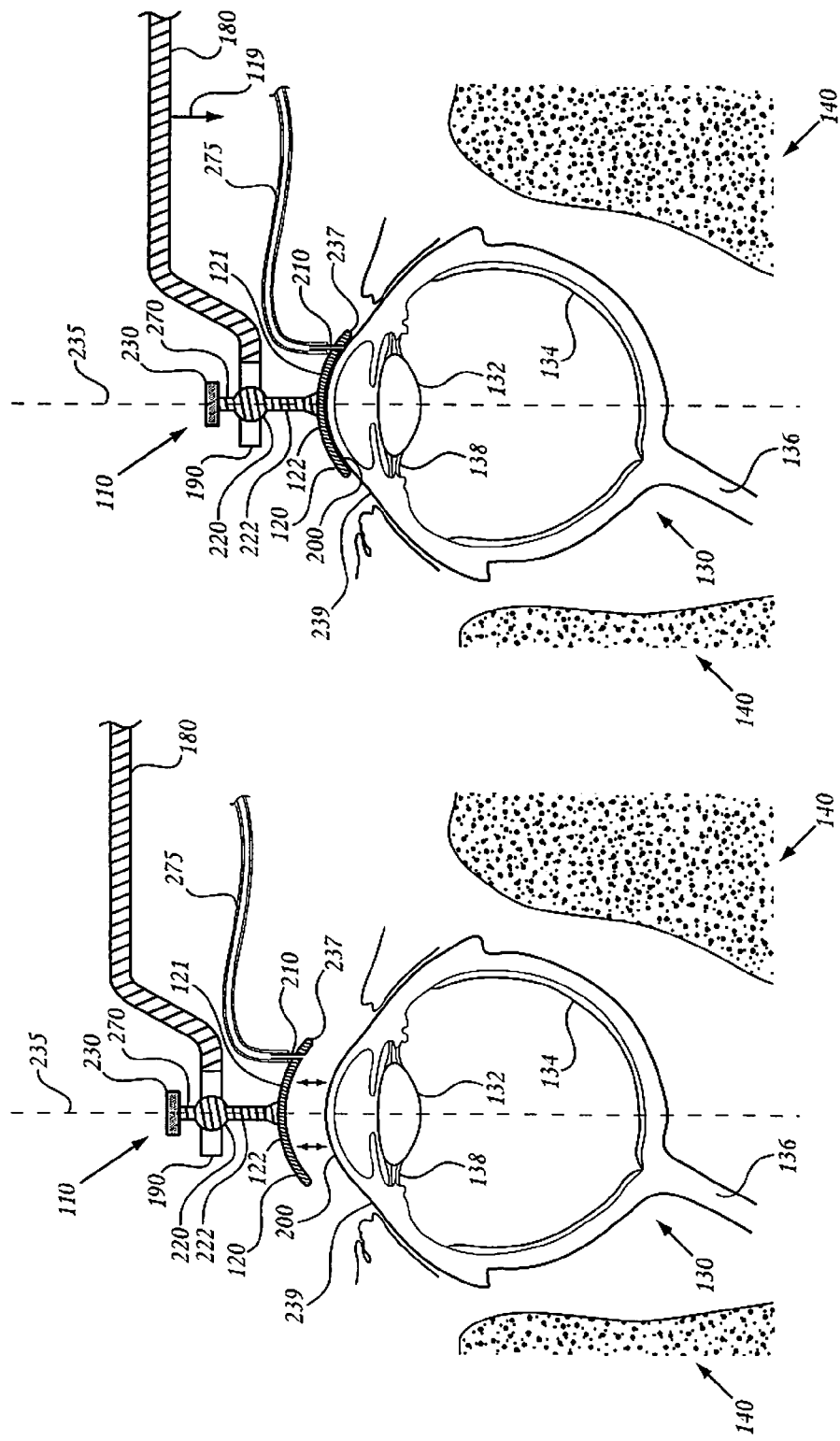

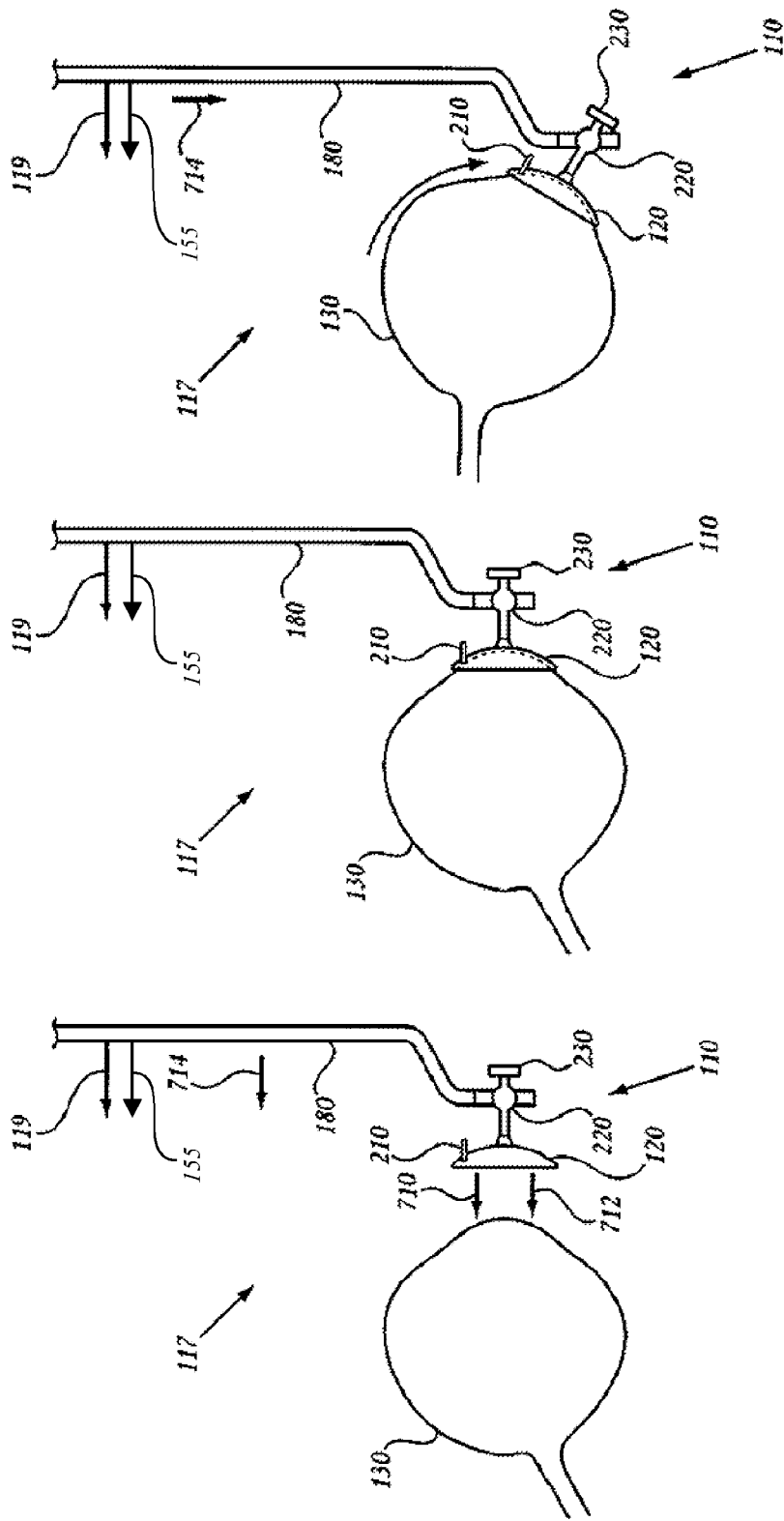

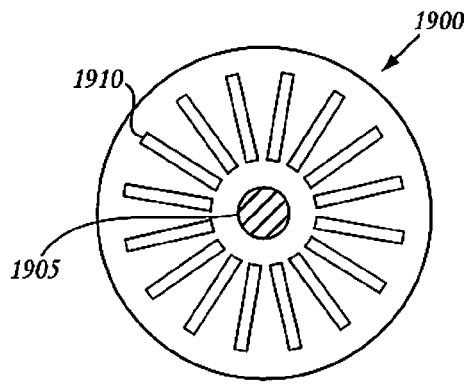
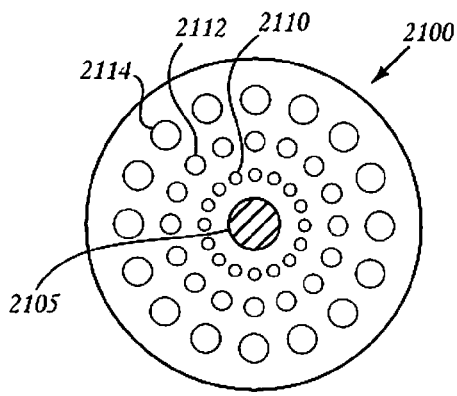
FIG. 19    FIG. 21
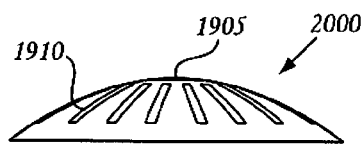
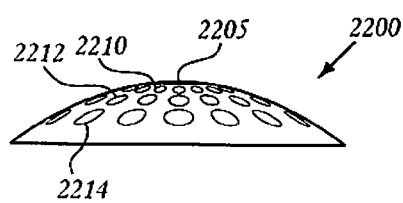
FIG. 20    FIG. 22
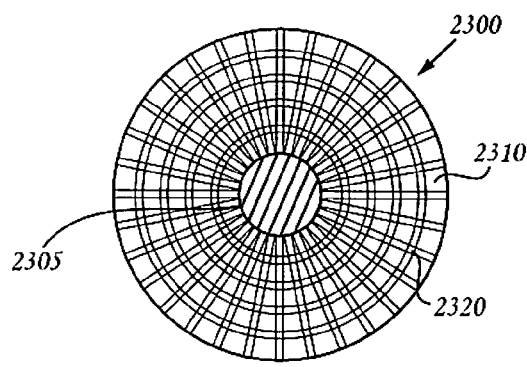
FIG. 23
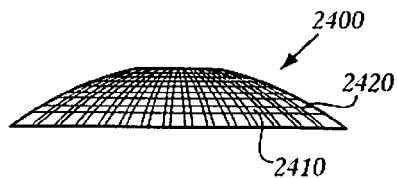
FIG. 24

SYSTEM AND METHOD FOR PERFORMING AN OCULAR IRRADIATION PROCEDURE

This application claims the benefit of priority to U.S. Provisional Patent Application No. 61/020,655 filed on Jan. 11, 2008, which is incorporated herein in its entirety by reference.

FIELD OF THE INVENTION

The present invention pertain s generally to a system and method for performing an ocular irradiation procedure on a patient's eye.

BACKGROUND

A number of treatment and surgery procedures, typically involving irradiating one or more selected targets in the eye, require a patient's eye to be stabilized or positioned prior to and/or during treatment. For example, refractive laser surgery involves ablating corneal tissue of the eye with an ultra-fast, ultra-short pulse duration laser beam, to correct refractive errors in a patient's eye. To achieve ablation, refractive laser surgery requires a laser beam to be precisely focused to a very small focal spot within the cornea. As such, the patient's eye must be stabilized, and either the laser system must be properly and precisely aligned with the patient's eye, or the patient's eye must be properly and precisely aligned with the laser system.

In order to achieve proper alignment of the eye of the patient relative to the laser system, the system alignment settings and operating parameters must be well defined, steadfastly maintained, and frequently verified. Accurate and precise refractive surgery requires the corneal tissue be photoablated when the eye is substantially stabilized or stationary. Patient comfort and safety are also a consideration when holding the eye stationary and conducting laser surgery. Likewise, ocular radiotherapy treatment requires the eye to be stabilized and dynamically positioned during treatment.

In order to achieve the goal of maximizing results while minimizing risks to the patient during such eye treatment, it is important to eliminate, or at least significantly reduce, as many system errors as possible. This includes the improper alignment of the patient's eye relative to the treatment system. Alignment errors may result from either a misconfiguration of the system, or from the patient's interaction with the system. Insofar as patient/system interaction is concerned, any voluntary or involuntary movement of the patient's eye during treatment can significantly alter the alignment of the eye relative to the treatment system. It is necessary, therefore, to hold the eye of the patient stationary during these procedures.

In addition to the operational issued discussed above, patient safety is also a concern. In particular, when the eye is in direct contact with the system, the magnitude of the interactive forces that are exerted on the eye are of concern. The variety of events that can cause these forces to exceed safety limits need to be avoided. Thus, there is a need for a system which can physically manipulate the position of the eye, prevent undesired eye movement during treatment, provide needed safety precautions, and function as a positional reference between the surface of the eye, selected internal anatomy of the eye (e.g., the macula or optic nerve), and the system. The present system is designed to meet these needs.

SUMMARY OF THE INVENTION

The invention includes, in one embodiment, a system for performing an ocular irradiation procedure on a patient's eye. The system includes (a) a head support for supporting the patient's head, (b) an eye-contact device attachable to the front portion of the patient's eye, to stabilize the position of the eye relative to the eye-contact device; (c) means for determining the position of the patient's eye, with such stabilized with respect to the contact device, and with the patient's head supported in the head support, in an external coordinate system, (d) a source of a collimated irradiation beam, and (e) a beam-positioning assembly for positioning the beam source in the external coordinate system such that the beam, when activated, is aimed along a selected path at a selected coordinate in the external coordinate system corresponding to a selected target region in the patient's eye.

The eye-contact device may include an internal concave eye-contact surface adapted to be placed against the front surface of a patient's eye, an external surface, a port in fluid communication with the contact surface, by which a negative pressure, e.g., a vacuum of between about 20 to 50 Hg, can be applied between the eye and the contact surface, to stabilize the position of the eye with respect to the contact device, and a connector carried on the outer surface of the device. In this embodiment, the system may further include a biasing mechanism operatively connected to the connector of the contact device for biasing the contact device against the eye with a force sufficient to the hold the contact device against the eye, when the eye is stabilized with respect to the device by application of a negative pressure between the eye and the device's contact surface. An exemplary force is between 1-25, typically 5-20, gram-force The determining means may include a position detector for determining the position of the contact device, and thus the position of the patient's eye attached to the contact device, in the external coordinate system. In this general embodiment, the position detector may include a plurality of beam elements mounted on the contact device, for directing beams in accordance with the position and orientation of the beam elements, sensors for detecting the directions of the beams, and a processor for determining from the detected beam directions, the position and orientation of the contact device in the external coordinate system.

The system may further include an eye-positioning assembly for moving the eye-contact device to place the device at a selected position in the external coordinate system, and the position detector may be operable to determine the position of the contact device in the external coordinate system, with such placed at said selected position. Thee ye-positioning assembly may be operable to adjust the angular position of the contact member with respect to the patient's head, and the position detector may detect an angle of a beam emanating from the contact member. The eye-positioning assembly may include an arm that is pivotally attached to the eye-contact member, and an arm control mechanism for controlling the movement of the arm in at least one direction in the external coordinate system, and the position detector may be operable to determine the position of the contact device in the external coordinate system from the position of the eye-positioning assembly arm in the external coordinate system.

The determining means includes a reference-beam light source operatively connected to the irradiation-beam source, for producing a reference light beam along a path coincident with the collimated irradiation beam produced by the irradiation beam source, and the beam-positioning assembly may be operable to place the irradiation beam source at a position such that the collimated light beam is aimed at the selected target region of patient's eye.

For use in treating macular degeneration in a patient eye, the beam source may be a source of soft collimated x-rays, and the beam-position assembly may be operable to position the beam source to direct a collimated x-ray beam at the macular region of the eye, along a path through an outer side region of the eye that makes an angle with an axis normal to the cornea of the eye, between about 5 and 45 degrees.

In another embodiment, the invention includes a method for performing an ocular irradiation procedure on a patient's eye, by the steps of: (a) supporting the patient's head in a head support, (b) attaching to the front of the patient's eye, an eye-contact device effective to stabilize the position of the eye relative to the contact device; (c) with the eye-contact device placed to a selected position, and with the patient's head supported in the head support, determining the position of a selected target region of the patient's eye in an external coordinate system, (d) positioning a source of a collimated irradiating beam in the external coordinate system such that the source beam, when activated, is aimed along a selected path at a selected coordinate in the external coordinate system corresponding to a selected target region in the patient's eye, and (e) activating the beam source.

Attaching step (b) may include placing against the front portion of the patient's eye, a concave contacting surface of an eye-contact device, and applying a negative pressure between the eye and the contact surface, thus to stabilize the position of the eye with respect to the contact device, and which further includes biasing the contact device against the eye with a force sufficient to the hold the contact device against the eye, wherein the position of the eye is stabilized with respect to the device. The negative pressure applied to the contact device may be between 20 mm Hg and about 50 mm Hg. An exemplary force is between 1-25, typically 5-20, gram-force.

The method may further includes, after attaching the eye to the eye-contact device, moving the contact device to place the device at a selected position in the external coordinate system, and step (c) may include determining the position of the ocular device in the external coordinate system, with such placed at its selected position. Moving the eye-contact device to place the device at a selected position in the external coordinate system may include directing an incident light beam onto a reflective surface of the contact member, detecting the angle of the beam reflected from said surface, and adjusting the angular position of the contact member until the incident light beam is coincident with the reflected light beam.

Determining the position of a selected target region of the patient's eye in an external coordinate system includes aiming a collimated light beam along a path coincident with the collimated electromagnetic beam produced by the beam source and positioning the light beam until it is aimed at the selected target region of patient's eye.

For use in treating macular degeneration in a patient eye, step (d) may include positioning a collimated x-ray beam source to direct a collimated x-ray beam at the macular region of the eye, along a selected path through an outer side region of the eye that makes an angle with an axis normal to and through the center of the cornea of the eye, of between about 5 and 45 degrees. The treatment method may include repeating steps (d) and (e) at each of a plurality of different paths of the collimated x-ray beam.

These and other objects and features of the invention will be more fully appreciated when the following detailed description of the invention is read in conjunction with the accompanying figures.

BRIEF DESCRIPTION OF THE FIGURES

The figures and the associated descriptions are provided to illustrate embodiments of the disclosure and not to limit the scope of the disclosure. Throughout the figures, reference numbers are reused to indicate correspondence between referenced elements. The figures are in simplified form and are not necessarily precise in scale. In reference to the disclosure herein, for purposes of convenience and clarity only, directional terms, such as top, bottom, left, right, up, down, over, above, below, beneath, rear, and front are used with respect to the accompanying figures. Such directional terms are not to be construed as limiting the scope of the invention in any manner.

FIGS. 2A-2B illustrate top views of an embodiment of a system for engaging the eye of a subject;

FIGS. 7A-7C illustrate a method of engaging and positioning an eye of a subject in accordance with one embodiment of the invention;

FIG. 19 is a frontal plan view of an embodiment of an eye-contact member with a plurality of radially extending slots emanating from the center of the eye-contact member;

FIG. 20 is a side view of the eye-contact member of FIG. 19 showing a plurality of radially extending slots emanating from the center of the eye-contact member;

FIG. 21 is a frontal plan view of an embodiment of an eye-contact member with a plurality of circular shaped apertures increasing in size and radially spaced from the center of the eye-contact member;

FIG. 22 is a side view of the eye-contact member of FIG. 21 showing a plurality of circular shaped apertures increasing in size and radially spaced from the center of the eye-contact member;

FIG. 23 is a frontal plan view of an embodiment of an eye-contact member with a grid of apertures within the eye-contact member;

FIG. 24 is a side view of the eye-contact member of FIG. 23 showing a grid of apertures within the eye-contact member;

DETAILED DESCRIPTION

Figure 1:
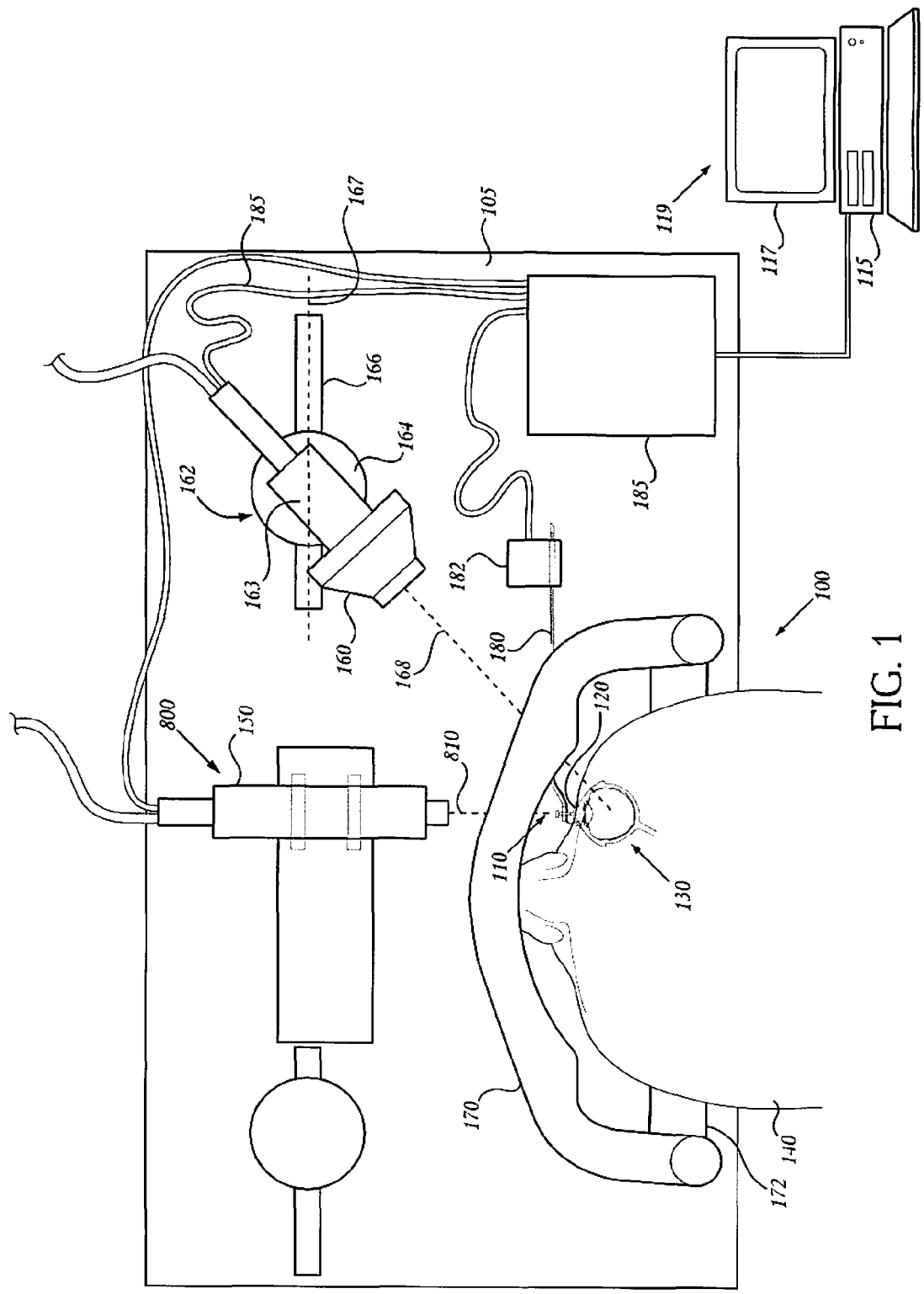
FIG. 1 illustrates a top view of one embodiment of a system for controllably positioning and/or stabilizing the eye of a subject for therapeutic treatment.

Reference will now be made in detail to disclosed embodiments of the invention, examples of which are illustrated in the accompanying figures.

I. Definitions

Unless otherwise indicated, all technical and scientific terms used herein have the same meaning as they would to one skilled in the art of the present invention. It is to be understood that this invention is not limited to the particular methodology and protocols described, as these may vary.

As used herein, "accommodation" refers to the ability to change focus from distant objects to near objects, which ability may tend to diminish with age.

The term choroid" refers to the highly vascular layer of the eye beneath the sclera.

As used herein, "ciliary muscle" refers to a muscular ring of tissue located beneath the sclera and attached to the lens via zonules.

As used herein, "conjunctiva" refers to the thin, transparent tissue covering the outside of the sclera. In some embodiments of the invention, reference is made to one or more devices or systems of the invention in contact with outer structures of the eye, such as the sclera. In these embodiments, it is to be understood that the device or systems of the invention may be in contact with the named structure, or may be in contact with the conjunctiva covering the structure.

As used herein, "cornea" refers to the transparent, avascular tissue that is continuous with the opaque sclera and semi-transparent conjunctiva, and covered by tear film, or corneal epithelium, on its anterior surface and bathed by aqueous humor on its posterior surface.

As used herein, "limbus" refers to the boundary where the cornea meets the sclera.

As used herein, "retina" refers to the light-sensitive layer of tissue that lines the inner back of the eye and sends visual impulses through the optic nerve to the brain.

As used herein "ocular disease" refers to a disease of the eye, including, but not limited to tumors, ocular degeneration, such as macular degeneration retinopathies, retinitis, retinal vasculopathies, diabetic retinopathies, diseases of the Bruch's membrane and the like.

As used herein, the term "reducing ocular disease" also encompasses treating and alleviating the ocular disease.

As used herein, "sclera" refers to the outer supporting structure, or "white," of the eye.

As used herein, the "front of the eye" refers at least a central portion of the cornea and may include surrounding structures, such as the sclera.

As used herein, the term "subject" refers to man or any animal that has eyes.

As used herein, "vitreous body" refers to the clear colorless transparent jelly that fills the eye posterior to the lens and that is enclosed by a hyaloid membrane.

As used herein, "zonules" refers to a circular assembly of radially directed collagenous fibers that are attached at their ends to the lens and at their outer ends to the ciliary muscle.

As used herein, the term "presbyopia," refers to the inability of the eye to focus sharply on nearby objects. Presbyopia is associated with advancing age and typically entails a decrease in accommodation. Introduction of treatment, e.g., laser ablation, according to any of the implementations described herein, preferably increases or facilitates an increase in accommodation, thereby mitigating effects of presbyopia.

The term "radiodynamic therapy" refers to the combination of collimated x-rays with a concomitantly administered systemic therapy.

The term "radiodynamic agents" is intended to have its ordinary and plain meaning, which includes, without limitation, agents that respond to radiation, such as x-rays, and agents that sensitize a tissue to the effects of radiation.

The term "photodynamic therapy" refers to a therapeutic or diagnostic method involving use of a photoreactive agent and radiation of a sufficient intensity and wavelength to activate the photoreactive agent. The activated photoreactive agent then, through emission of energy, exerts a therapeutic effect or allows for diagnosis through detection of emitted energy.

The term "photodynamic agents" is intended to have its plain and ordinary meaning, which includes, without limitation, agents that react to light and agents that sensitize a tissue to the effects of light.

The term "radiation therapy" is intended to have its well-accepted meaning and can also refer to any treatment performed with an energy source.

As used herein, "treatment" refers to any manner in which one or more of the symptoms of a disease or disorder are ameliorated or otherwise beneficially altered. Treatment also encompasses any therapeutic use of the systems herein.

As used herein the term "external coordinate system" refers to a coordinate system that is fixed, such as a room or the fixed element, e.g., base, of a system component. It typically provides a common set of coordinates to place in registry, devices which are moving relative to one another, or which cannot be accurately placed at pre-selected position in the coordinate system, such as a patient's head.

Diagnostics can also be performed with any type of energy source or treatment described herein and may be referred to as "radiation diagnostics."

The "position" of an object, such as an eye-contact member, in an external coordinate system refers to the position of some known point on the object, as defined by the coordinates of that point in the coordinate system. The coordinate system may be, for example, a three-dimensional Cartesian coordinate system, in which the object's position is defined by x, y, and z coordinates, or a spherical coordinate system in which object's position is defined by radius and angle coordinates.

A "biasing force" refers to a force exerted against a patient's head (or eye), typically expressed in terms of units of gram-force, i.e., the force exerted by the earth's gravity acting on a gram mass.

A "beam-directing element" refers to an element capable of reflecting an impinging beam, such as a light, microwave, or ultrasound beam, onto a detector, or an element that itself is capable of producing a beam, such as a light beam that is aimed at one or more beam detectors. The beam-directed elements are attached to an eye-contact device or assembly for purposes of determining the positions of the beam-directing elements, and thus the position of an eye-contact device or assembly to which they are attached, in an external coordinate system.

A "reservoir" or "vacuum reservoir" refers to an internal chamber or chambers, e.g., array of fluid-carrying tubes, by which a negative pressure applied to an eye-contact device can distributed over the contact surface of an eye-contact member.

A "pivot joint" refers to a coupling between two mechanical elements that allow of the elements to shift, typically in an angular direction, with respect to the other element. Exemplary pivot joints include ball and universal joints, both of which provide multiple degrees of freedom, e.g., degrees of angular motion, between the two elements.

II. System for Stabilizing the Eye and for Performing an Ocular Irradiation Procedure A system in accordance with the present invention is shown in FIG. 1 and is generally designated 100. The system 100 functions as an ocular interface useful for one or more of the following functions: i. controllably stabilizing the eye; ii. physically manipulating eye position; iii. limiting eye from movement during treatment; iv. positionally referencing the surface of the eye, its internal anatomy, and/or the system (e.g. to an external coordinate system) v. providing fiducials relative to the eye and relative to treatments performed as well as monitoring positioning of the fiducials relative to the eye; vi. maintaining corneal lubrication during treatment; vii. provide a mechanism to align a treatment device and continuously signal adequate alignment or misalignment. Substantial or total controllable stabilization of the eye is advantageous for a wide variety of treatment, diagnostic, and/or surgery procedures as described in detail below.

The system 100 includes a platform 105 which allows stationary attachment of one or more of the components of the system, as described below, such that precise positional information regarding the components of the system relative to a known coordinate system (e.g., an external coordinate system) are capable of being determined. The system defines a reference or external coordinate system in which the components of the system are registered, such that all of the points can be positioned and aligned with one another at known positions in the external coordinate system. The components of the system described may be automatically positioned in the coordinate system by a computer interface, as will be described below. Alternatively, some of the components of the system 100 may be manually positioned. In another embodiment, one or more of the components of the system 100 are positioned automatically, and one or more of the components of the system 100 are simultaneously positioned manually.

System 100 includes an eye-contact device 110 having an eye-contact member or surface 120 that reversibly engages or couples to the front an eye 130 of a subject 140 (e.g., FIGS. 2A and 2B). Contact device 110 is connected to a control arm 180 which is part of an eye-positioning assembly 182 for placing the contact device at a selected position in the external coordinate system, as will be seen below. Preferably, control arm 180 is pivotably connected to contact device 110 as described below. In some embodiments, the control arm releasably detach from the contact device or the eye-contact member in case of sudden patient movement, as will be described below with respect to FIGS. 4A-4D. The eye-contact member 120 engagement with the eye 130 maintains the eye in substantially stabilized or immobilized position. Alignment of the eye can be accomplished with the use of the laser device 150, which can provide alignment of the contact device 110 as described in further detail below. Thus, FIG. 1 illustrates a preferred embodiment of the patient ocular interface system 100 of the invention.

With continuing reference to FIG. 1, system 100 is a patient ocular interface for treatment of an ocular structure with a treatment device 160. As noted, the system includes an eye-contact device 110 adapted to maintain an eye 130 in a substantially stable position. In one embodiment of the invention, the contact device is configured to provide an indication to a sensor that the eye 130 is in substantially the first position during delivery of treatment from device 160, located outside the eye. In a preferred embodiment, the system includes a communication link 185 that communicates information between the contact device 110 and the treatment device 160, the information being indicative of a position of the eye and determining a characteristic of one or more parameters of the treatment device 160.

Treatment device 160 may include any of a number of devices that provide therapeutic treatment to the eye. Such therapeutic treatments are described in detail below. In general, device 160 is a source or a collimated irradiation beam directed along a selected axis or path 168, such as a source of electromagnetic radiation (e.g., ablating optical energy, thermal optical energy, low level therapeutic optical energy, or radiofrequency energy), ultrasound, and magnetic implementations. The treatment device 160 includes, in one general embodiment, is an energy emitting source, such as an electromagnetic laser (e.g., a diode laser) and/or radiation source having a predetermined wavelength, an ultrasound device with a predetermined pulse, a cautery device with a predetermined setting that interacts with desired parts of the eye, a radiofrequency module, an ultrasonic component, and combinations thereof. Device 160 can further be a surgical implement or manipulator; for example, a surgical probe for intraocular brachytherapy or superficial brachytherapy can be held in position in a similar manner as device 160 with the exception that the surgical implement is placed inside the eye. In one preferred embodiment of the invention, the treatment device 160 is a source of a collimated irradiation beam, such as a portable source of soft-x-ray beams generated by directing soft x-rays from a conventional x-ray source through a collimator. For purposes of illustration, device 160 will be referred to herebelow as a source 160 of a collimated irradiation beam.

Device 160, in some embodiments, can be a diagnostic device. It may be desirable to hold an eye in a position to obtain fine detailed diagnostic information about the eye such as OCT, scanning laser ophthalmoscopy, CT scan, MRI, or any other device which may send energy into the eye and be dependent on steadiness of the structure and/or a known coordinate reference.

A beam-positioning assembly 162 in the system is designed to position the beam source 160 in the external coordinate system such that the beam, when activated, is aimed along a selected path, corresponding to the beam axis 168, at a selected position in the external coordinate system corresponding to a selected target region of the patient's eye. As seen in FIG. 1, the beam-positioning assembly includes a swivel mount 164 on which the beam source is mounted for rotation about an axis 163, and a linear guide 166 on which the swivel mount can travel along an axis 167. Although not shown here, the "height" position of the beam source can be adjusted along axis 163, so that the beam from the beam source is at the same height as a target region in the patient eye. The angular position of the beam source position on swivel mount 164 and the linear position of the swivel mount on guide 166 can be adjusted manually, or preferably, is under the control of stepper or servo motors which themselves are controlled by a control unit 115, described below. In addition, the mounting on the beam source on swivel mount 164 may be through a connection, such as a ball or universal joint, that allows the angle of the beam-source collimated beam, represented by axis 168, to be adjusted "up" or "down" with respect to a the plane representing by platform 105, for directing the beam at slight upward or downward angles into the eye.

Figure 8A:
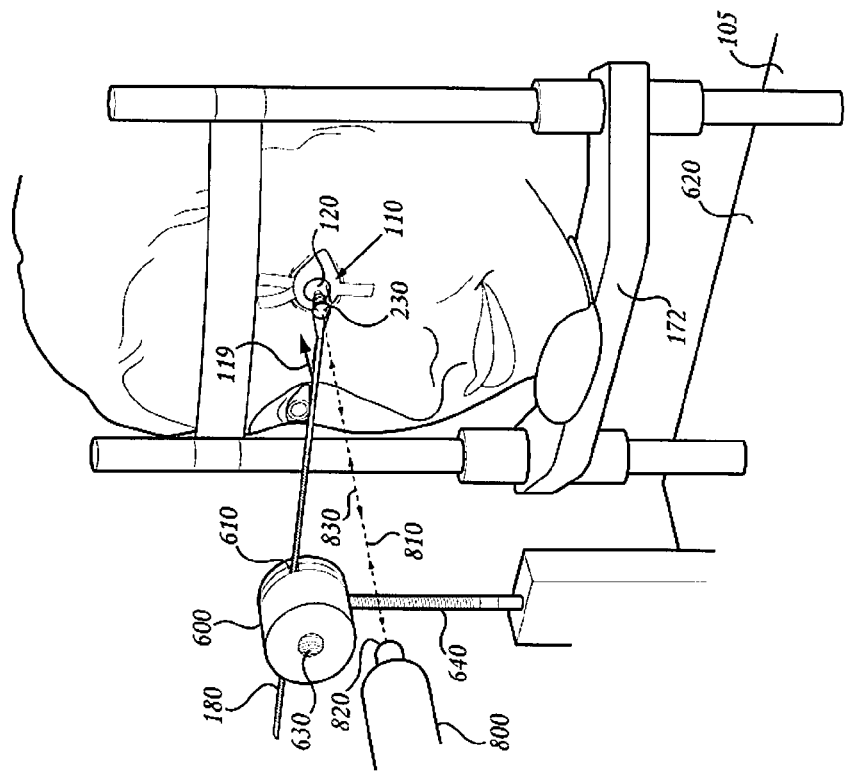
FIGS. 8A-8B illustrate perspective views of the contact device out of alignment with the system (FIG. 8A) and in substantial alignment with the system (FIG. 8B) in accordance with preferred embodiments of the invention.
Figure 8B:
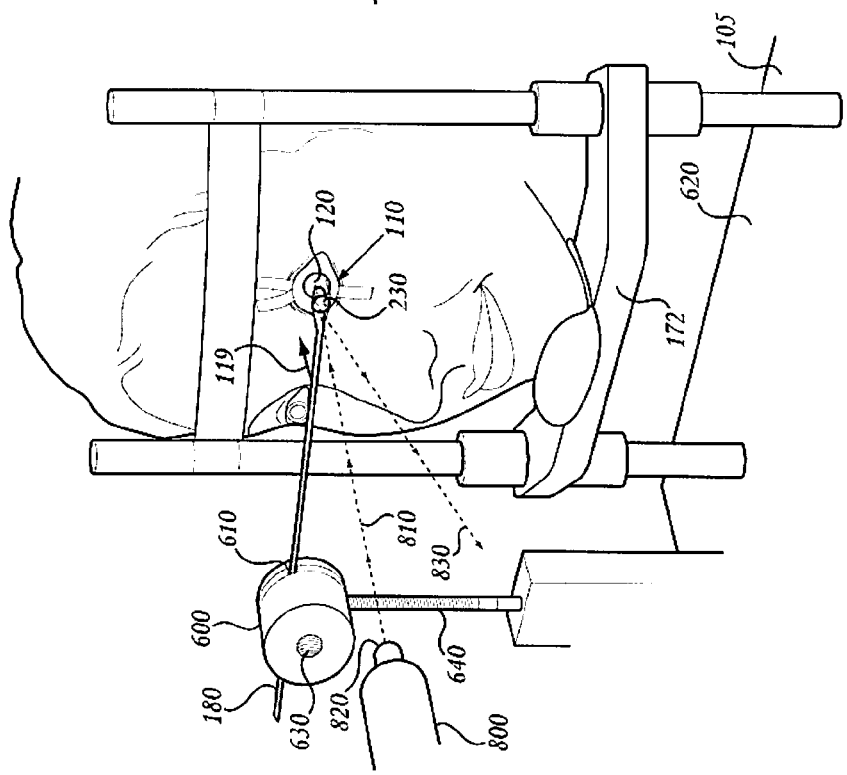

A head support or support 170 for stabilizing the head of subject 140 is included in system 100, and includes a chin rest 172 (FIGS. 8A and 8B). Head support 170 is, in the embodiment of the invention illustrated in FIG. 1, attached to the platform 105, e.g., by permanent or releasable attachment. In one embodiment, head support 170 includes a motorized control assembly with position sensors which can be selectively activated to move and reconfigure the head support. Further details of the support, and its function is supporting a patient's head, is described below with respect to FIGS. 8A and 8B.

Also included in the system are means for determining the position of a selected target region of the patient's eye in the external coordinate system, with the patient's eye stabilized with respect to the eye-contact device, and the contact device moved to a selected position. The coordinate or coordinates thus determined are used by the beam-positioning assembly to move the beam source in the external coordinate system such that the collimated irradiation beam, when activated, is aimed along a selected path at the selected eye coordinate corresponding to the selected target region of the patient's eye in the external coordinate system.

Figure 6A:
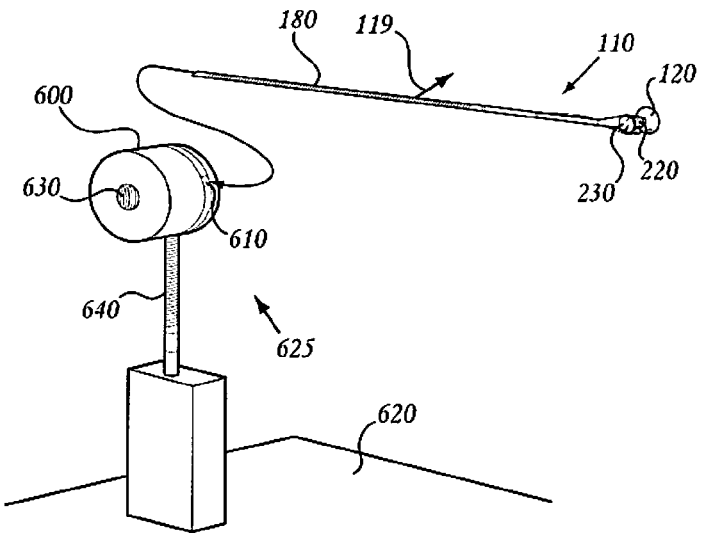
FIGS. 6A-6C depict perspective views of an contact device and control arm being reversibly engaged with the system in accordance with one embodiment of the invention.
Figure 6B:
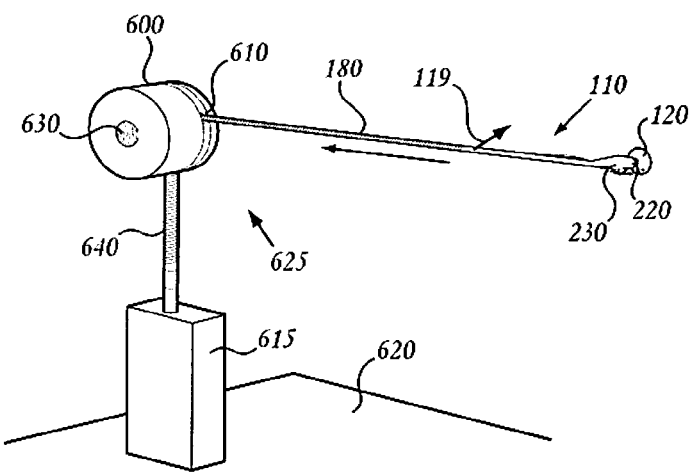
Figure 6C:
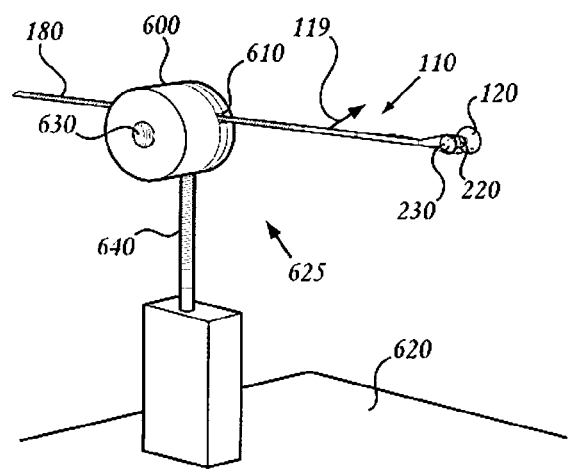

In a first general embodiment, the means for determining the position of a selected eye target includes an eye-positioning assembly illustrated in FIGS. 6A-6C, for positioning the eye-contact device at a selected orientation or alignment, a detector for determining when the eye-contact device has been moved to the selected orientation, and position sensors in the eye-positioning assembly for determining the coordinates of the eye-contact device when moved to the selected orientation. In particular, FIGS. 8A and 8B depict a mechanism by which the contact device 110 can be used to align the eye with laser alignment system 800, including laser device 150. Optionally, the alignment mechanism also directly aligns a treatment system, such as a radiotherapy system (not shown) in which the radiotherapy system directs its energy toward the eye in relation to the alignment system. Laser pointer beam 810 (which is collinear with the therapeutic beam in some embodiments) is emitted from laser system 800 through a collimator opening 820 and reflects off the surface of beam-directing mirror 230 of the contact device 110. In the non-alignment case depicted in FIG. 8A, the laser pointer beam 810 will not reflect off the surface of mirror 230 collinearly with the collimator opening 820, but will be off-axis, as shown by reflection beam 830. The orientation of the laser system 800 and/or the contact device 600 can be manually or automatically adjusted by direct visualization of the location of the reflection beam 830 or by sensors that detect the location of the reflection beam 830 and adjust the laser system 800 to bring the laser reflection beam 830 into alignment. In the case where the laser pointer is in fact aligned (FIG. 8B), the laser pointer beam 810 is reflected, and the laser reflection beam 830 is substantially collinear with the laser pointer beam 830.

The eye-positioning assembly used to position the eye-contact device at a selected orientation, as just described, is illustrated in FIGS. 6A-6C. The figures show perspective views of the contact device 110 attached to a control arm 180 in the positioning assembly, indicated at 625, which is being fed into slot 610 of drive mechanism 600. In some embodiments, the contact device 110 of the system can be attached to a coupling component to hold the eye in place. The coupling component can be attached to the treatment device, but preferably, as shown in FIGS. 6A-6C, it is attached at a location separate from the radiotherapy device, such as a drive mechanism 600 that is attached to a table or platform 620 which holds the treatment device.

Contact device 110 is preferably disposable such that a separate (e.g. disposable) contact device 110 is employed for each subject and/or use. Alternatively, contact device 110 may be nondisposable and be treated, e.g., with anti-infective agents, prior to being utilized in multiple subjects' eyes. Drive mechanism 600 is fixed to base 620 through connector 640, which is may robotically controlled, but preferably manually controlled, and has a known coordinate system. In one embodiment, drive mechanism 600 is fixed in a known, or predetermined, location with respect to the head positioning system (not shown) and/or the eye of the subject (not shown) and/or the positioning system of the radiotherapy device. Push button 630 allows free manual positioning of contact device 110 into and/or out of slot 610. Thus, as illustrated in FIG. 6A, the control arm 180 is not engaged with the drive mechanism 600. In FIG. 6B, the control arm 180 is partially engaged with the drive mechanism 600. And in FIG. 6C, the control arm 180 is fully engaged with the drive mechanism 600 and is fixed in a known, or predetermined location, which allows the eye of the subject to be fixed in a known, or predetermined location, when contact device 110 engages the eye.

Although not shown, the eye-positioning device includes internal position sensors operable to detect the position of the end of arm 110 in the external coordinate system, in accordance with movement of the arm in a y direction.

In one embodiment of the invention, spatial registration is used in combination with the system to record and monitor the three dimensional spatial position of the contact device 110 at all times, relative to a known reference point. One method of accomplishing the registration is through the use of a spatially encoded control arm 180, which tracks the position of the contact device 110. The control arm 180 holds the contact device 110 at one end, and is mechanically stabilized or fixed to the platform 620 at the other end. The control arm 180 engages drive mechanism 600, allowing at one degree of freedom and up to three or more degrees of freedom, and may employ encoding devices to accurately determine the position and orientation of the contact device 110 relative to the platform. The control arm 180 also allows movement and positioning of the contact device 110. The control arm 180 is used to accurately and reproducibly position the contact device 110. The positional information of the contact device 110 is then conveyed to localization software for registration of the position of the eye. The vertical or y position of the control arm can likewise be adjusted through movement of a drive 615 on which drive mechanism 600 is movably mounted, allowing both the x and y position of the control arm, and the eye-contact device attached to the control arm, to be accurately determined in the external coordinate system. In particular, the system functions to move the control arm to place the eye-contact device at a desired orientation, by the mechanism shown in FIGS. 8A and 8B, and then determine the position of the eye-contact device at this orientation from the known arm coordinates.

As will be discussed further below, the motion arm includes a biasing mechanism or element, such as a spring or magnetic element, that operates to bias the arm and an eye-contact device supported at the end of the arm against the patient. The biasing element, which is represented by force arrow 119 in FIGS. 2B, 6A-6C and 8A and 8B, may be a coil spring within or attached to mechanism 60 or a magnetic biasing mechanism, such as an electromagnetic mechanism that swings the arm in the direction of the patient with a desired biasing force of preferably between 1-25 grams, typically 5-20 grams. This mechanism for securing the contact device to the eye and stabilized the position of the eye is discussed below with reference to FIGS. 8A and 8B.

In a second and related general embodiment, the eye-contact device is equipped with a plurality of position indicators that are capable, in combination with detectors located in the external coordinate system, to locate the position of the contact device in the external coordinate system. This type of tool-tracking system, has been described for use in image guided surgery, where it is necessary to place a movable surgical tool, and typically also pre-op patient images, in a common surgical frame of reference containing the patient. In the present application, the position indicators may be three or more beam-directing elements designed to reflect external positioning beams, e.g., microwave beams from known-position beam sources to known-position beam detectors, with the position of the contact device being determined by a processor operatively linked to the beam detectors. Alternatively, the beam-directing elements in the eye-contact device can be equipped with a plurality of LEDs mounted on the device for directing, for example, a plurality of beams at known-position detectors to determine the position coordinates of the contact device in the external coordinate system. Such tool registration systems have been described, for example, in U.S. Pat. Nos. 7,139,601, 7,302,288, and 7,314, 430, all of which are incorporated herein by reference in their entirety.

In a third general embodiment the position-determining means takes the form of a collimated light-beam assembly, including a laser light source and one or more optical components, such as a half-silvered mirror, for aligning the laser beam with the collimated irradiation beam produced by beam source 160; such that the two beams are essentially coincident, along the same axis 168. In this embodiment, the beam-positioning assembly is moved with respect to the patient's eye until the laser beam is aimed directly onto the selected target region of the patient's eye, e.g., the macula region at the central rear portion of the retina. As can be appreciated, this will place the selected target region of the eye in registry with the therapeutic irradiation-beam; that is, the laser beam acts as a reference beam that functions to place the eye in the same frame of reference (coordinate system) as the irradiation beam.

More generally, the spatial registration and guidance of the contact device 110 may be through optical or electromagnetic sensor detection. In general, cameras or other detectors are mounted either on the system, or optionally in the treatment room, and are used to track and register the position of the eye or contact device 110. Cameras or detectors are then able to determine and record the three dimensional position of the contact device 110 in real time, and therefore the position of the eye as it is positioned. A calibration process can be used to determine the relative spatial position of the contact device to a known reference frame, as well as in combination with optional images. The calibration information can be stored in a reference file on the computer and used by a software program.

With continued reference to FIG. 1, system 100 also includes a processor or control unit 115 which has a graphical user interface 117 for receiving instructions from, and presenting information such as alignment and system functionality data to, a system operator. Further, the control unit 115 is in electronic communication with one or more of the other components of system 100 described above, e.g., the motors controlling the beam-positioning assembly, the motors controlling the eye-positioning assembly, and sensors, detectors and beam sources for determining the position of the eye-contact device in the external coordinate system, as described above. An electrical cable may be used to connect control unit 115 to the additional components. Alternatively, the connection between the control unit 115 to one or more of the components of the system is wireless.

Referring now to FIGS. 2A-2B, top-down views of the contact device 110 being reversibly and controllably coupled to the cornea 200 and/or limbus and/or sclera 239 of the eye 130 is schematically illustrated. The eye 130 includes a cornea 200 and a lens 132 posterior to the cornea 200. The eye 130 also includes a retina 134, which lines the interior of the rear surface of the eye 130. The retina 200 includes a highly sensitive region, known as the macula, where signals are received and transmitted to the visual centers of the brain via the optic nerve 136. The retina 200 also includes a point with particularly high sensitivity known as the fovea. The eye 130 also includes a ring of pigmented tissue known as the iris 138. The iris 138 includes smooth muscle for controlling and regulating the size of an opening in the iris 138, which is known as the pupil. The eye 130 resides in an eye socket 140 in the skull and is able to rotate therein about a center of rotation.

The eye-contact device 110 functions to stabilize the eye in a first position to provide interactive support (e.g. stabilization and/or controllable movement) for the eye while the eye is being treated. The contact device 110 includes a cup or eye-contact member 120 which contacts eye 130. The contact member 120 can be positioned on the eye in a variety of positions, and is therefore useful in a wide variety of ocular treatment procedures. In one embodiment, the eye-contact member is in at least partial contact with the cornea 200. In a preferred embodiment, as illustrated in FIG. 2B, the eye-contact member substantially covers but not necessarily touches the cornea of the eye 130 when in operative position. In a related embodiment, the eye-contact member substantially covers the cornea, but only makes contact with the limbus of the eye on the periphery of the eye-contact member 120, such that the cornea is covered, but is not in direct physical contact with the surface of eye-contact member 120. The contact member 120 is preferably a curved structure that is substantially centered on the axis 235 with the periphery 237 of the contact member 120 in contact with the sclera 239 and overlying the cornea 200. Thus, the curved contact member 120 is positioned to create an interior cavity between itself and the cornea.

The curved contact member 120 is preferably shaped with a concave eye-contact surface that will substantially conform to the anterior surface of the cornea 200 of the eye 130. The contact surface of the contact member 120 preferably has a radius of curvature that is greater than about 5 mm. In one embodiment of the invention, the radius of curvature of the inner surface of the eye-contact member 120 is 7.38 mm. Likewise, in a preferred embodiment, the radius of curvature of the outer surface of the eye-contact member 120 is preferably 7.38 mm. It will be appreciated that a 1:1 ratio of inner and outer curvatures minimizes or eliminates refraction of energy through the eye-contact member 120 in certain embodiments of the invention; in this embodiment, the contact member 120 is a simple cup for the eye 130. Alternatively, the inner and outer curvatures may differ to permit desired focusing or diffraction of energy as it is transmitted through the eye-contact member 120. In some embodiments, the contact member 120 is produced in a variety of shapes, one or more of which can be chosen for a given patient depending on his or her specific anatomy.

As contemplated by the present invention, the eye-contact member 120 can be made of a number of materials well known in the art. In an exemplary embodiment of the invention, the contact member 120 is made from poly(methylmethacrylate), or PMMA. A certain degree of rigidity, or hardness, of eye-contact member 120 is of use in physically coupling with the eye and with the pivot which attaches to the control arm as described in further detail below. However, the eye-contact member 120 includes, in certain embodiments, a certain degree of flexibility, or softness, such that the eye-contact member 120 has a degree of flexibility, but still retains an arcuate shape in its resting position. In some embodiments, eye-contact member can break away from the contact device at a predetermined position along connector 222, as described in greater detail below.

Preferably, the eye-contact member can be fashioned from any suitable material with attention to biocompatibility. Thermoset and/or thermoplast PMMA are contemplated by the present invention and are supplied by a number of sources, such as Perspex CQ (ICI Derby, England). Teflon and tantalum are also noted. It is also possible to coat eye-contact member 120 with biocompatible materials if elements of the eye-contact member 120 are not biocompatible. In some embodiments, the eye-contact member 120 contains pigments or dyes. In particular embodiments, the eye-contact member 120 is coated or impregnated with bioactive substances including anti-inflammatory agents/immunomodulating agents and/or anti-infective agents. Particular eye-contact members will contain radiopaque, radioactive, fluorescent, NMR contrast or other reporter materials.

With continued reference to FIGS. 2A and 2B, the contact member forms, with a back plate 121 of the contact device, an internal reservoir 122 by which a negative pressure (partial vacuum) applied to the device, through a vacuum port 210, is distributed across the contact surface of the device, as can be appreciated. The vacuum port is connected to a suitable vacuum source though a tube 275. In the embodiment illustrated in FIGS. 2A and 2B, the vacuum port 210 is positioned through the eye-contact member 120 such that an air or fluid communication space is formed through eye-contact member 120 to allow air trapped between eye-contact member 120 and the anterior surface of the cornea 200 of eye 130 to be reversibly removed, thereby reversibly engaging the eye-contact member 120 with the anterior surface of the cornea 200. In an alternative embodiment not shown, vacuum port 210 is attached to connector 270 which can contain a hollow lumen along axis 235 through eye-contact member 120 such that air between eye-contact member 120 and the anterior surface of the cornea 200 is capable of being reversibly removed as described above. Vacuum or suction assistance is useful for locating and adhering the scleral lens base on the eye 130 of the subject and securing the contact device 110 to the subject's eye 130. Once in a desired treatment position, the contact device 110 can couple with the system 100 during the treatment procedure, as described below. Following treatment, the contact device 110 can be decoupled from the system 110 and removed from the subject.

In one preferred embodiment, negative pressure applied to the eye, for example, a negative pressure of 20-50 mm Hg, is effective to stabilize the position of the eye on the device, that is, substantially prevent movement of the eye with respect to the device, but by itself is not sufficient to hold the eye-contact device on the eye. Rather, the contact device is secured to the eye by a biasing force acting to bias the device against the patient's eye, acting in combination with the negative pressure applied to the eye by the device. In the embodiment illustrated, the contact device is secured to the eye by the biasing force acting through arm 180, where the negative pressure applied to the contact device functions to prevent the eye form moving with respect to the device. As noted above, the contact device is typically biased against the eye with a force of between about 1-25, typically 5-25 grams, by a biasing spring, electromagnetic force, or the like. The advantage of this system is that the negative pressure applied to the eye can be substantially less than that which would be required if the vacuum alone were acting to hold the device to the eye, and this substantially lower negative pressure increases comfort and reduces irritation and deformation of the front portion of the eye. The biasing force is illustrated in the figures, e.g., FIG. 2B, by an arrow 119, which indicates the direction of action of the force in the figures.

When the eye-contact member 120 contacts eye 130, negative pressure is applied to remove air from between the eye and contact member, to stabilize the position the eye 130 with respect to the contact member. A primary vacuum fitting is in fluid communication with the air passage. A vacuum line 275 is connected to the vacuum port 210. Additionally, a vacuum pump is in air or fluid communication with the vacuum line 275 for evacuating the air trapped between eye-contact member 120 and the corneal surface 200. Collectively, the vacuum port 210, line 275, and pump (not shown) constitute a primary vacuum subsystem. The degree of strength of the vacuum required to seal can be varied, and preferably controllably and continuously monitored, by the system of the invention. In one embodiment of the invention, between about 0.5 mm Hg and about 50 mm Hg are utilized to provide the negative pressure effective to stabilize the position of the eye with respect to the contact member 120. Preferably, the vacuum is between about 20 mm Hg and about 50 mm Hg. More preferably, the vacuum force applied is about 25 mm Hg and is monitored by pressure sensors and/or by directly monitoring the vacuum source. In some embodiments, the pressure is held passively, for example, by a bladder. The bladder can be produced such that it can apply a given maximum pressure.

In one embodiment of the invention, one or more pressure sensors are placed onto the contact surface of eye-contact member 120 such that the pressure of the force being applied by the vacuum, and causing contact between eye-contact member 120 and the corneal surface 200 can be monitored and selectively adjusted. The adjustment of the pressure can be automated. Throughout the treatment procedure, e.g., radiotherapy treatment, data from the pressure sensors can communicate to the control unit 115 via a communication link 185. During the treatment and positioning procedure as illustrated in FIGS. 7A-7C, and discussed in detail below, the interactive forces that are generated between the eye-contact member 120 and the drive mechanism used to moveably rotate the eye can be monitored by pressure sensors. The force magnitudes experienced by the pressure sensors, and the differentials between the force magnitude, can used to determine the magnitude and direction of the forces exerted against the eye 130 during the positioning and/or treatment procedures. In this way, the operation of the system 100 is monitored to ensure eye safety, and to minimize the risk of unwanted damage or injury to the eye 130. Specifically, whenever a predetermined force threshold is reached, either in the direction or the magnitude of the forces exerted on the eye 130, further movement of the subject's eye is prevented by the control unit 115.

When activated, the primary vacuum subsystem evacuates air through vacuum port 210. The evacuation of air creates a negative pressure at the interface of the eye-contact member 120 and the anterior surface of the cornea 200 and/or sclera. The present invention also contemplates use of one or more sensors to detect whether a vacuum is formed. In the event the eye-contact member is not properly seated on the eye 130, the partial vacuum will not form. In this case, an error message is displayed for the system operator on the graphical user interface 117 of the control unit 115 of FIG. 1. The error message may be an audio message, a visual message, or a combination of the two. In one embodiment of the invention, suction is used to initially engage the contact device 110 to the eye 130, and following initial engagement, the suction is removed and the contact device 110 remains on the eye throughout the treatment procedure. In another embodiment of the invention, suction is used to initially engage the contact device 110 to the eye 130, and following initial engagement, the suction force is maintained throughout the treatment procedure.

By engaging the contact member 120 with the eye 130, the eye 130 becomes fixed in a first position, the patient unable to move the contact member with intra-ocular movements. The contact member can, however, be moved using control arm 180; the movement by the control arm rotates the eye through the eye-contact member. Thus, one embodiment of the invention includes substantially stabilizing the eye 130 in a selected position with the eye-contact member 120.

With continued reference to FIGS. 2A and 2B, contact device 110 also includes a pivot joint or connector 220 which accommodates pivot movement between the contact member and positioning arm 180, as the arm moves the contact device to a desired orientation in the external coordinate system. In a preferred embodiment, pivotable connector 220 is a spherical or ball pivot joint which allows rotation in three dimensions. As seen best in FIGS. 3A and 3B, positioning arm 180 may be releasably coupled to the contact device through a stem-and-socket arrangement which fastens the end of arm 180 to a socket formed in ball joint 220.

Eye-contact member 110 also includes a beam-directing mirror 230 or other detector or sensor, which in combination with the laser system 150, allows the position and rotation of the eye to be placed at a desired orientation or position in the external coordinate system. As shown, the mirror 230 is parallel to the eye-contact member 120 and provides a reflective surface to align the contact device 110 to the eye and to the treatment device. The position of the mirror 230 also provides a known reference to the subject's corneal apex by virtue of the contact member fitting closely to the eye upon application of some vacuum. The alignment of the eye-contact member with a reference laser beam will be described below with reference to FIGS. 8A and 8B.

In one embodiment, the mirror 230 includes a reflective material that reflects at least one wavelength of light. In some embodiments, the characteristic of a treatment device 160, e.g., a radiation beam, is determined by the information and includes at least one of a trajectory of the radiation beam and an emit/not-emit status. In some embodiments, the communication link to the treatment device 160 is an optical link. In some embodiments, the contact device 110 is adapted to align the treatment device 160 with a visual axis of the eye. Some embodiments further include a camera that visualizes a position of the eye relative to the contact device 110. In some embodiments, the camera detects movement of the eye and communicates data relating to the eye's movement with imaging software.

In other embodiment, the eye-contact device includes a plurality of fiducials and/or a plurality or beam-directing elements by which the position of the eye-contact member, and thus the position of a patient eye stabilized in the contact member, in an external coordinate system can be determined. As noted below, multiple fiducial arrays or multiple beam-directing arrays may be monitored by camera or beam-sensing detectors for determining the position of the fiducial or beam-directing elements in the external coordinate system.

In some embodiments, the eye-contact member 110 is attachable to a surface external to the eye. In some embodiments, the eye-contact member 110 is mechanically linked to a eye-position assembly that includes control arm 180. In some embodiments, the contact device 110 is engaged with the eye 130 by docking the contact device 110 into position on the eye 130 (e.g., by the physician) so that the center of the holder has a center in common with the limbus of the eye. This common center is a step in assuring that the treatment device is aligned with the optical or geometric axis of the eye. With knowledge of the center of the limbus in combination with an eye model, the treatment device 160 can then be directed about a treatment axis and center of the limbus to deliver treatment, e.g., radiation, to a target region of the eye, e.g., the retina. The position of the eye 130 can also be tracked by a treatment system 160, e.g., a radiotherapy system.

Some embodiments further include a material that is transmissive of energy through the contact device 110. In some embodiments, the radiation beam comprises laser light. In some embodiments, the radiation beam comprises x-rays. Some embodiments further include a material that is transmissive of energy through at least a portion of the contact device 110. Energy sources contemplated by the present invention include radio waves, microwaves, infrared light, visible light, ultraviolet light, x-rays and gamma rays.

In some embodiments, the energy comprises laser light. In some embodiments, the energy comprises x-rays. In an alternative embodiment, the energy comprises protons for use in proton therapy or gamma rays for use in gamma ray therapy. In some embodiments, the eye-contact member 120 includes a transmissive portion that transmits a first wavelength of electromagnetic radiation from outside to inside the eye.

In some embodiments, the first portion is reflective of a second wavelength of electromagnetic radiation. Thus, the eye-contact member 120 may selectively allow transmission of one or more preferred wavelengths of electromagnetic radiation. Eye-contact member 120 may selectively reflect one or more wavelengths of electromagnetic radiation. In one embodiment of the invention, eye-contact member 120 selectively allows transmission of one or more preferred first wavelengths of electromagnetic radiation, and also selectively reflects one or more second wavelengths of electromagnetic radiation. In one embodiment, the portion selectively reflecting and/or selectively transmitting one or more wavelengths of electromagnetic radiation is centrally located in the eye-contact member 120. In another embodiment, the portion selectively reflecting and/or selectively transmitting one or more wavelengths of electromagnetic radiation is off-centered, on the eye-contact member. In one embodiment, the portion selectively reflecting and/or selectively transmitting one or more wavelengths of electromagnetic radiation is peripherally located in and/or on the eye-contact member 120. In some embodiments, at least one of the plurality of wavelengths of electromagnetic radiation comprises laser light beams. In some embodiments, at least one of the plurality of wavelengths of electromagnetic radiation comprises x-ray beams.

Figure 3A:
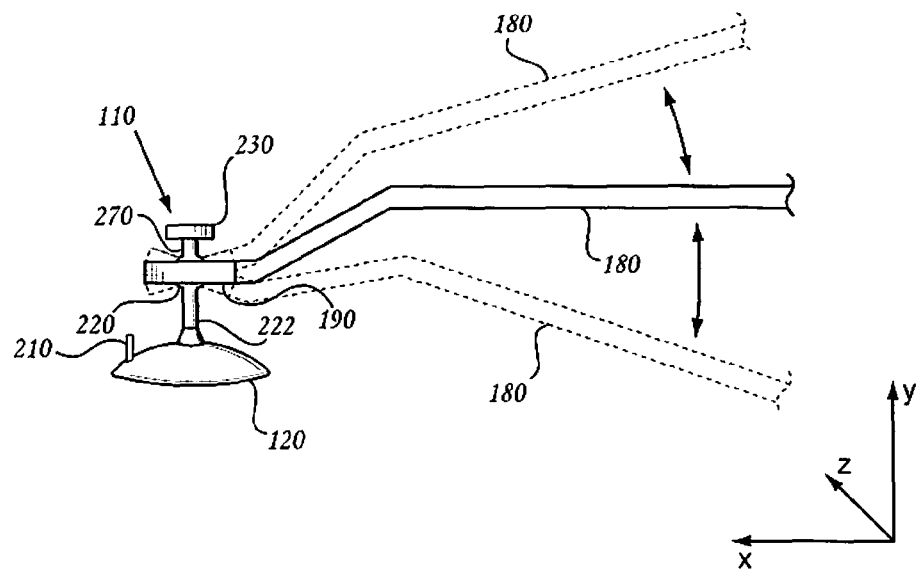
FIGS. 3A-3D illustrate top and perspective views of the contact device and pivotable control arm in accordance with preferred embodiments of the invention.

FIG. 3A is a side view of contact device 110 illustrating the pivotability of control arm 180 around the spherical pivotable connector 220. The control arm/contact device assembly includes a swiveling tiltable head 190 carrying a conical divot or the like providing a good mating fit. In the embodiment shown, the head 190 of control arm 180 is tilted with respect to a spherical coupling 220 positioned within the conical divot of head 190. The coupling includes a hollow interior within control head 190 that is located at the end of control arm 180 or other connector that snap-fits onto and rotatably rides upon a mating connector 220. In one embodiment of the invention, the swiveling head 190 is designed to coincide with the center of mass of the contact device. The swiveling and tiltable head 190 permits a wide range of motion of the eye-contact member 120 when the spherical pivot is inserted into the hollow interior of head 190 of control arm 180. Thus, movement of the control arm 180 in the X, Y, and/or Z directions as illustrated in FIG. 3A, permits the contact device to be controllably positioned. Importantly, when the contact member 120 and holder are fixed with vacuum to the eye as shown in FIG. 2, a greater degree of friction is created between the spherical pivot 220 and the head 190 of control arm 180 so that the eye moves very little after vacuum is applied. Moreover, the eye pivots around a point toward its posterior as it is pulled by intraocular muscles which rotate the eye around this posterior point. When the eye-contact member is coupled to the eye, the eye and the holder are locked together at the pivot point of each. The intra-ocular muscles cannot move the contact member around its pivot which is the only way the contact member can move. Arm 180 can move contact member 120 through spherical bearing 220. Similarly the patient's face or head can move the contact member by translation of their head or body which would similarly induce a movement about spherical pivot 220. However, the muscles of the eye cannot move contact member 120 when it and the eye are held together. As a result of such rotational articulation and subsequent coupling, including the friction between the hollow interior of head 190 and spherical pivotable connector 220, the contact device 120 can be positioned on an eye and stabilized. Such rotational positioning of the contact device and coupling of the pivot points also allows the mirror 230 of the contact device to be aimed or aligned with the system within a known coordinate system.

The friction between head member 190 and pivotable connector 220 can be increased or decreased as desired by varying the surface of the pivotable connector 220 and/or head member 190. For example, to decrease the friction between the pivotable connector 220 and the head member 190, a metal may be used which can be electropolished by a predetermined amount to provide the desired extent of smoothness. Alternatively, one or both of the surfaces of pivotable connector 220 and head member 190 may be dimpled on either a micro or macro level using known surface finishing or machining techniques to increase or decrease friction accordingly. Additionally, a liquid lubricant, such as glycerin can be applied to the surface of the pivotable connector 220 to reduce the friction at the head member 190/pivotable connector 220 interface, as desired.

Distal end of the control arm 180 has little or no free movement as its x-y position is controlled manually or automatically. However, once the holder and the eye are coupled to one another, the eye can be positioned by positioning the arm 180 in the X-Y directions or positioning the patient's head. Arm 180 can have some flexibility in the Z direction, acting as a cantilever, so that the holder 120 on the eye is not completely rigid. Alternatively, a mechanism is provided which controllable adjusts the contact member in the z direction.

Figure 3B:
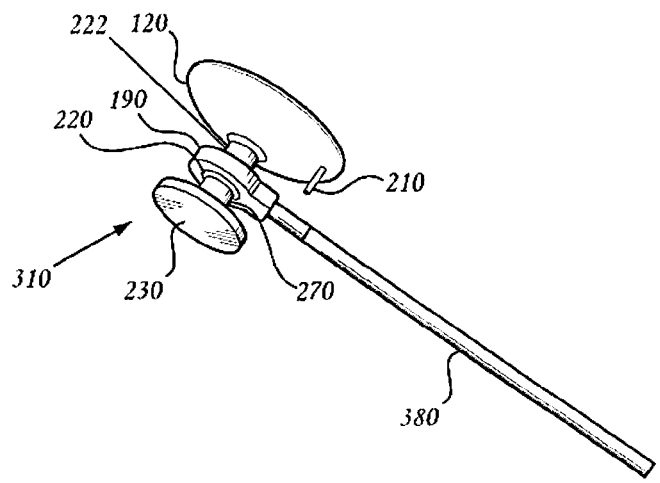

FIG. 3B is a perspective view of contact device 310 showing a straight control arm 380 for mechanically linking contact device 310 to a system for controllably positioning an eye for treatment. In one embodiment, the eye-contact surface of eye-contact member 120 contacts the sclera of eye 130. In another embodiment, the eye-contact surface contacts the cornea of eye 130. In yet another embodiment, the eye-contact surface of eye-contact member 120 is in contact with both the cornea and the sclera. In some embodiments, the contact device 110 includes a portion which is at least partially opaque or reflective to x-ray energy. In some embodiments, the eye-contact holder 110 includes at least a portion that is at least partially transparent to x-ray energy. In some embodiments, the contact device 110 is configured to apply a suction to the eye 130 through vacuum port 210. Some embodiments further include a contact device 110 that is configured to contact the eye 130 and maintain a position of the eye. In the embodiment of the invention illustrated in FIG. 3B, the control arm 180 is generally cylindrical. As used herein, the term "generally cylindrical" is not limited to a perfectly cylindrical surface, but instead is understood to include any faceted or other column or like structure (e.g., an octagonal cylinder, a hexagonal cylinder, etc.). The material strength of the arm is controllable such that a thin arm has greater spring than a thick arm. The thicker arm can therefore apply greater force to the eye when the subject is positioned in the holder 120. In some embodiments of the invention a strain gauge is used to measure the resistance and/or change in resistance as the control arm 180 is deflected during positioning and/or stabilization of the contact device 110.

Figure 3C:
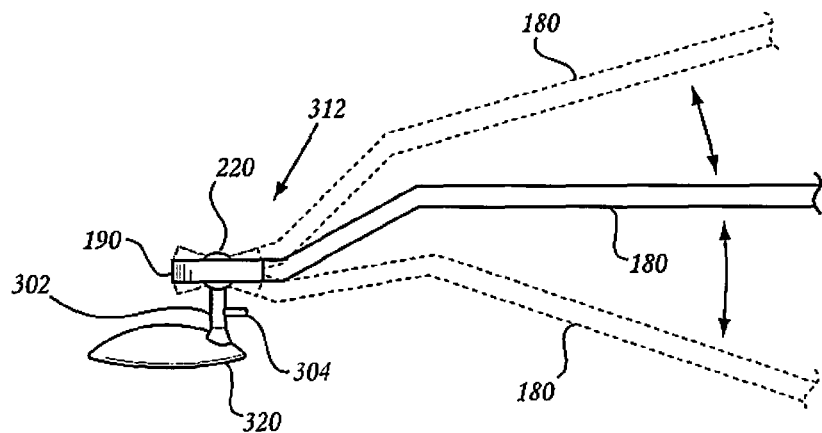
Figure 3D:
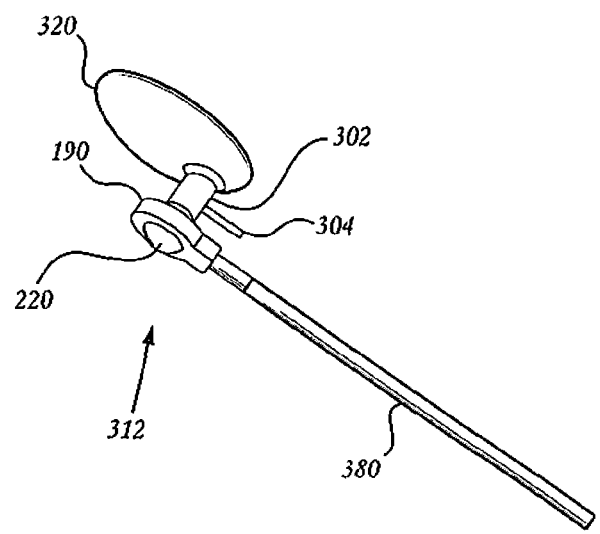

FIGS. 3C and 3D illustrate alternative embodiments of contact devices 312 pivotably connected to control arms 180 and 380, respectively. As can be seen in FIG. 3C, eye-contact member 320 is connected to spherical pivot 220 through connector 302 off-center of contact member 320. In the embodiment shown, the head 190 of control arm 180 is tilted with respect to a spherical coupling 220 positioned within the conical divot of head 190. The coupling includes a hollow interior within control head 190 that is located at the end of control arm 180 or other connector that snap-fits onto and rotatably rides upon a mating connector 220. Vacuum port 304 is in air or fluid communication with connector 302 which is in air or fluid communication with a space formed through eye-contact member 320 which is in air or fluid communication at the eye/contact device interface when the contact device 312 is positioned on the eye of a subject.

FIG. 4 illustrates an exploded view of the contact device 110 with each component of one embodiment of the contact device 110 separated. Eye-contact member 120 can be reversibly coupled to pivotable connector 220 at coupling points 224, 226 which can be reversibly coupled to mirror 230 at coupling points 228, 229. Such coupling may include interlocking snaps, glue, welding, magnets, etc. The mirror can be painted, sprayed or applied with a vacuum deposition process. The coupling preferably includes one or more magnets, as illustrated in FIGS. 4B-4C.

Figure 4A:
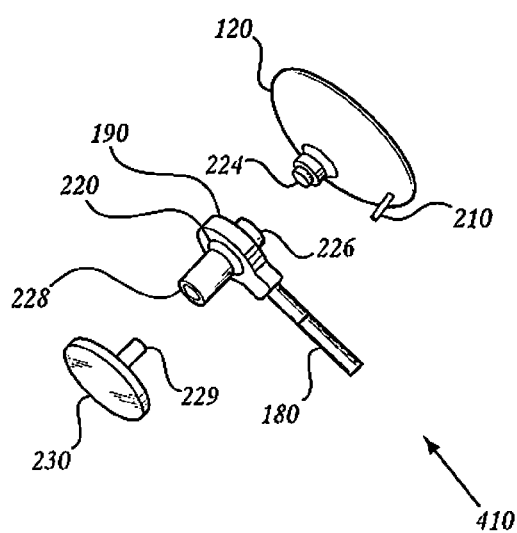
FIGS. 4A-4F depict an exploded view (FIG. 4A), connecting views (FIGS. 4B-4E), and another view (FIG. 4F) of the contact device in accordance with certain embodiments of the invention.
Figure 4B:
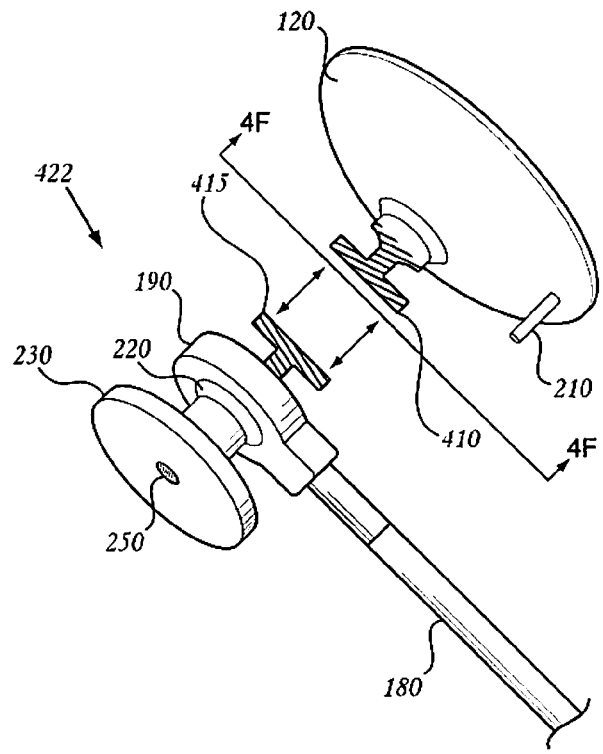
Figure 4C:
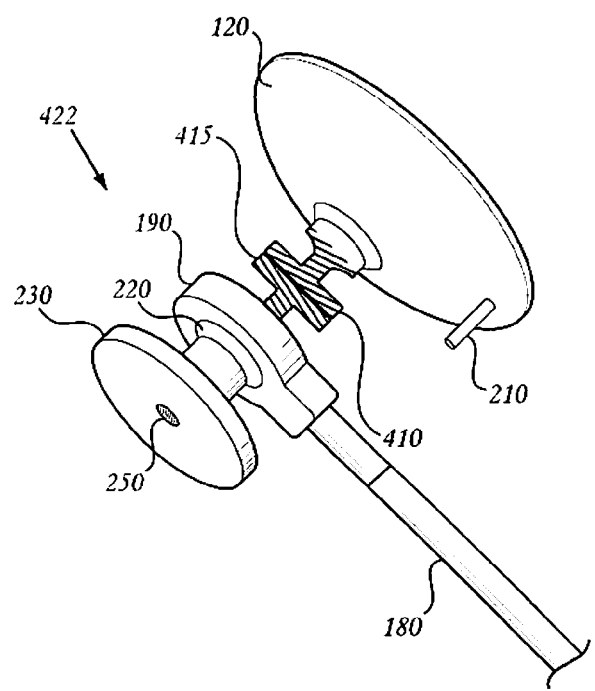

More generally, FIGS. 4B and 4C and 4D and 4E illustrate two embodiments of an eye contact device in accordance with one aspect of the invention in which an eye-contact member is releasably coupled to a positioning arm through releasable coupling members carried on each component of the assembly. In FIGS. 4B and 4C, the assembly is indicated at 422 and includes an eye-contact member 120 having a first magnet 410 thereon, and an arm-attachment member 190 carrying a second magnet 415 thereon. As seen in FIG. 4C, as the first coupling member 415 is brought toward the second coupling member 410, the two coupling members couple the eye-contact member 120 with the spherical pivot 220 which mates with the head 190 of control arm 180 such that the eye-contact member 120 is connected to the system. This allows the eye-contact member 120 to move together with control arm 180 and therefore be in a known position within the coordinates of the system. Thus, in operation, the eye-contact member 120 may be positioned on the eye of a subject prior to magnetically coupling the two coupling members 410, 415. In an alternative embodiment, the eye-contact member 120 is positioned on the eye of a subject following magnetically coupling the two coupling members 410, 415. The magnetic coupling can also be used as a safety feature in that the magnets become uncoupled when force is applied in a direction which is not co-linear with the perpendicular axis to the magnets.

Figure 4D:
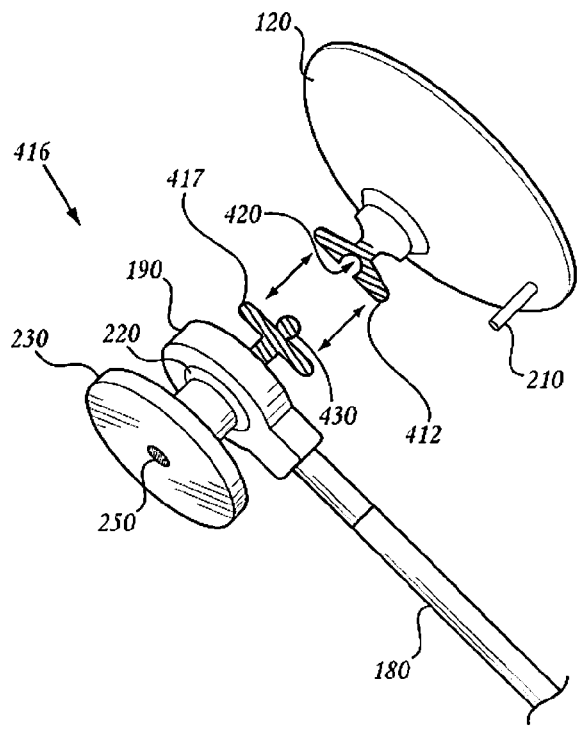
Figure 4E:
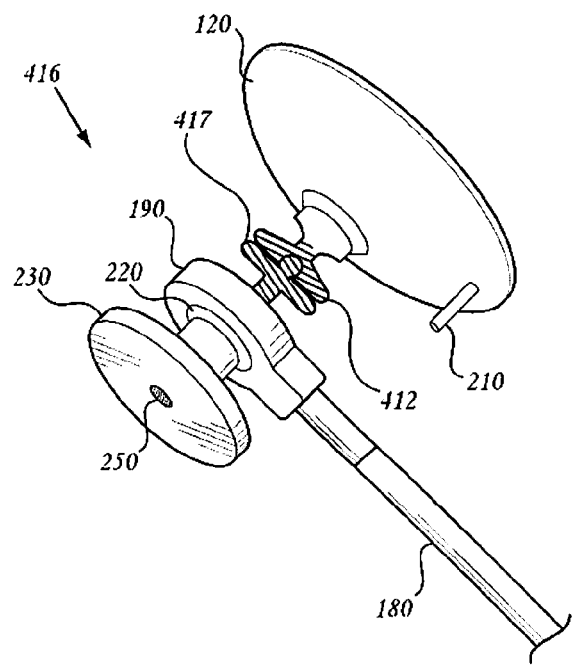

In a similar manner, FIGS. 4D-4E illustrate a snap fit coupling or mechanical coupling between the eye-contact member 120 and control arm 180 in a second embodiment of an eye-contact assembly 416. In FIG. 4D a snap or plurality of snaps is disposed on the first snap coupling member 417 for snap coupling with a snap or plurality of snaps on the second snap coupling receiving member 412.

In the embodiment illustrated in FIGS. 4D-4E, eye-contact member 120 is attached to second snap coupling receiving member 412, which includes a built-in divot 420. In this embodiment, the divot 420 includes a female receptacle, such as the illustrated conical depression. However, as used herein, a divot also refers to any other male or female receptacle, or the like. The divot 420 is capable of receiving a correspondingly sized and shaped mating tip 430 which is coupled to the first snap coupling member 417, which is thereby coupled through spherical pivot 220 to control arm 180. Such a control arm 180 is useful for registering the actual physical location of the subject's eye prior to, during, or following a selected treatment procedure. The registration can be accomplished using known coordinates within the system, or by obtaining images. Such images are typically stored in memory of an image-guided treatment computer workstation.

As seen in FIG. 4E, as the first snap coupling member 417 is brought toward the second snap coupling receiving member 412, the two coupling members couple the eye-contact member 120 with the spherical pivot 220 which mates with the head 190 of control arm 180 such that the eye-contact member is connected to the system. This allows the eye-contact member 120 to move together with control arm 180 and therefore be in a known position within the coordinates of the system. Thus, in operation, the eye-contact member 120 may be positioned on the eye of a subject prior to snap coupling the two coupling members 410, 415. In an alternative embodiment, the eye-contact member 120 is positioned on the eye of a subject following magnetically coupling the two coupling members 410, 415. That is, the releasable coupling members in the assembly are deformable, typically plastic, members with complementary interlocking shapes.

The snap fit or magnetic fit is not only of structural importance but can provide for an emergency breakaway mechanism if the subject's eye needs to move out of the restraint system shown in FIG. 1, as described in detail below. In a preferred embodiment, the releasable coupling members couple the eye-contact member to the arm with a release force sufficient to allow the device and a patient eye stabilized therein to be moved by the arm, and to release from one another when an above-threshold force is applied to the eye, e.g., by sudden eye movement, or abrupt arm movement, so that the eye is protected from injury that could result from sudden relative movement between the eye and contact member. The release force, that is, the force required to release the two components, may be in the same range, but typically somewhat greater than the biasing force used in biasing the contact device against the patient's eye, e.g., in the range 10-100 grams.

Figure 4F:
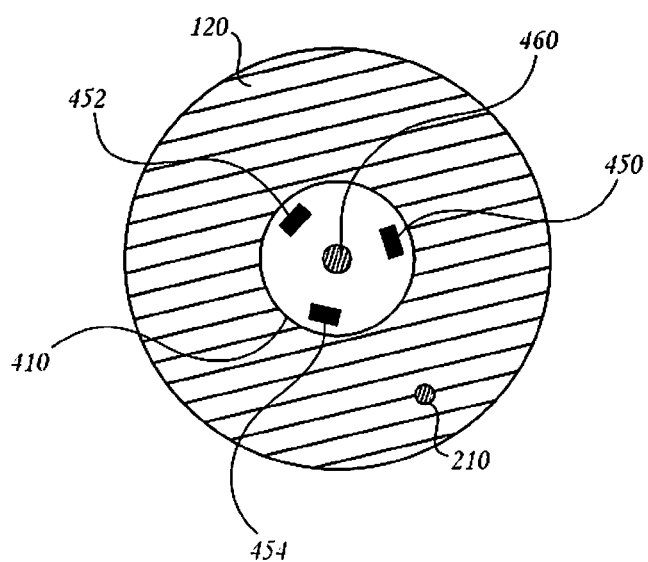

In one embodiment of the invention, one or more pressure sensors are positioned on coupling member 410, as illustrated in FIG. 4F. When the control arm 180 is mechanically engaged with the eye-contact member 120, the second magnetic coupling member 415 will contact one or more pressure sensors of which pressure sensors 450, 452, 454 are exemplary. Preferably, when in contact with second magnetic coupling member 415, the pressure sensors 450, 452, 454 lie in a plane that is substantially parallel to the plane of the first magnetic coupling member 410. As illustrated in FIG. 4F, the pressure sensors 450, 452, 454 are each positioned an equal distance from the center point of the first magnetic coupling member 410. Also shown in FIG. 4F is the position of the pressure sensors 450, 452, 454 relative to each other. Specifically, the three pressure sensors 450, 452, 454 are equidistant from each other, i.e., positioned 120 degrees apart. In an alternative embodiment of the invention, a plurality of pressure sensors are positioned on the second magnet coupling member 415.

In operation of this embodiment of the present invention including pressure sensors, once the eye-contact member 120 is positioned on the eye, and the control arm 120 is coupled to known coordinates within the system, the control arm 180 is moved through a "docking" procedure whereby the control arm 180 is moved to engage with the eye-contact member 120. During this docking procedure, the two magnetic coupling members 410, 415 are engaged. As intended by the present invention, the two magnetic coupling members 410, 415 are dimensioned to precisely match and reversibly couple to each other with the pressure sensors positioned therebetween. During the docking procedure, the interactive forces that are generated between the control arm 180 and the eye-contact member 120 are monitored by the pressure sensors 450, 452, 454. It can be appreciated by those skilled in the art that the force magnitudes experienced by the pressure sensors 450, 452, 454, and the differentials between the force magnitudes, can be used to determine the magnitude and direction of the forces exerted against the eye during the docking procedure. In this way, the operation of the system is monitored to ensure patient safety, and to minimize the risk of unwanted damage to the eye. Specifically, whenever a predetermined force threshold is reached, either in the direction or the magnitude of the forces exerted on the eye, further movement of the control arm 180 toward the eye-contact member 120 is prevented by the control unit. In one embodiment, when the threshold force is reached, the control arm 180 can only be moved in a direction away from the eye-contact member 120.

In yet another embodiment, when a predetermined force threshold is reached during the docking procedure or during treatment, such as when the subject moves out of position, the eye-contact member 120 can break away from control arm 180 such that patient safety is ensured. In this embodiment of the invention, if the interactive forces that are generated between the control arm 180 and the eye-contact member 120 reach a predetermined level, the magnetics or snaps may be controllably decoupled to permit the contact device 120 to break away or disengage from control arm 180. Simultaneously, when a predetermined level of interactive force or magnitude is reached, and the contact device 120 is disengaged from the control arm 180, the treatment or diagnostic procedure may be terminated.

In a similar manner, in accordance with another embodiment of the invention, when the control arm 180 is used to positionably rotate the eye in a controlled manner, pressure sensors 450, 452, 454 monitor the interactive forces that are generated between the control arm 180 and the eye-contact member 120. The force magnitudes experienced by the pressure sensors 450, 452, 454, and the differentials between the force magnitudes, can be used to determine the magnitude and direction of the forces exerted against the eye during the positioning procedure. In this way, the operation of the system is dynamically monitored to ensure patient safety and to minimize the risk of unwanted damage to the eye throughout the eye positioning and stabilization procedure. Specifically, whenever a predetermined force threshold is reached, either in the direction or the magnitude of the forces exerted on the eye, further movement of the control arm 180 is prevented by the control unit. In a related embodiment, whenever a predetermined force threshold is reached, further movement of the control arm 180 is prevented by the control unit, and the coupling, e.g., snap or magnetic coupling, between the control arm 180 and the contact device 120 is disengaged, decoupled or permitted to break away to ensure patient safety.

In one embodiment of the invention, when the predetermined force threshold described above is reached, the magnetic field between the two magnetic coupling members 410, 415 is turned off to allow the eye-contact member 120 to decouple from the control arm 180. In another embodiment, the treatment system is turned off when the predetermined force threshold described above is reached. In yet another embodiment, when the predetermined force threshold described above is reached, the magnetic field between the two magnetic coupling members 410, 415 is turned off to allow the eye-contact member to decouple from the control arm 180, and the treatment system 160 is turned off or prevented from being turned on such that the safety of the eye is continuously monitored and dynamically maintained throughout the eye positioning and/or treatment procedures.

In one embodiment the entire contact device 110 is molded as a single component. The contact device 110 includes, in one embodiment, an optical or other communication between the system 100 and the eye 130 by inhibiting movement of the subject. The contact device contains, in some embodiments, one or more of a radiotransmitter, a laser pointer, and/or features which can be captured on a camera so that the eye can be located in three-dimensional space.

Referring again to FIG. 4A, the contact device 110 contains, in some embodiments, a mirror 230. The mirror 230 can function as a beam reflector to indicate alignment or misalignment of the laser device 150 and/or the treatment device 160, e.g., a radiotherapy device. As the contact device 110 is positioned in contact with the eye, a proper engagement and alignment between the contact device 110 and the system is achieved. To this end, the laser light source 150 that is mounted on the platform is used to verify and monitor proper alignment. The light emanating from the light source is used to create a pattern of reflected light that is observable by the system operator, or in some embodiments, by an automated system. Referring now to FIGS. 8A-8B, an exemplary path of reflected light 830 is shown relative to the path of the source light 810. Importantly, when the pattern of reflected light 830 is reflected directly back along the path of the source light 810, the contact device 110 is properly engaged and aligned with the system. If, however, the contact device 110 is not properly or fully aligned with the laser 800, the path of reflected light 830 will be displaced or distorted from its preferred orientation. In this situation, as shown in FIG. 8A, the path of reflected light 830 relative to the path of the source light 810 emanating from the distal end 820 of laser 800 is indicative of an improper alignment. Further, the system operator can observe the misaligned path of reflected light directly, or on the graphical user interface, and properly align the contact device 110.

For example, the mirror 230 will reflect a light such as a laser pointer or an LED. The light originates on the laser device 800 and/or treatment device, and its reflection from the mirror 230 is indicative of the direction of the mirror relative to the laser device 800 and/or treatment device. The mirror 230 can be parallel to the surface of the cornea, and therefore, a beam perpendicular to the mirror is approximately perpendicular to the cornea. If a lumen, such as the lumen 250 as shown in FIGS. 4B-4F through the center of the mirror is present, and the eye-contact member 120 is transmissive of light at its center, a perpendicular beam to the cornea will travel through the optical or geometric axis of the eye and reach the center of the posterior pole of the eye. The lumen notwithstanding, the beam being reflected from the mirror 230, also represents the optical axis of the eye.

In some embodiments, the mirror 230 is a so-called "hot mirror" or a "cold mirror" in which the mirror 230 reflects some wavelengths and transmits others. For example, a "hot mirror" can reflect an infrared laser pointer and transmit visible light so that the patient or treating physician or a camera will be able to see through the lens. A "cold mirror" will transmit infrared and reflect visible so that a visible laser pointer can be reflected while infrared can be transmitted; cold mirrors can be used, for example, in cases where it is desired to utilize an infrared fundus camera during treatment.

As noted above, in some embodiments, contact device 110 can include material that is radiotranslucent, or that permits at least some radiation to pass. In some embodiments, the radiotranslucent material of the coupling device can be configured to permit the passage of the therapeutic x-ray beams during treatment. For example, the contact device can engage the eye to maintain position of the eye, and the x-ray beams can be directed to target eye tissue with a trajectory that passes through at least a portion of the contact device 110. Accordingly, a treatment planning system can plan x-ray beam trajectories without significant consideration of where the contact device engages or is positioned on the eye.

In some embodiments, the contact device 110 can include material that is radiopaque, or that reduces or limits the transmission of radiation. In some embodiments, the radiopaque material of the contact device 110 can be configured to limit transmission through the material of radiation, such as, for example, x-ray beams. For example, the contact device 110 can engage the eye to maintain position of the eye, and x-ray beams that are directed to target tissue of the eye will not be permitted to pass through, or transmission of the x-ray beams through the material will be substantially limited, the contact device 110. In these embodiments, the contact device 110 can be used as a shield for critical structures of the eye (e.g., the lens, the optic nerve, the cornea, and so forth) by limiting radiation exposure to these structures.

Figure 5A:
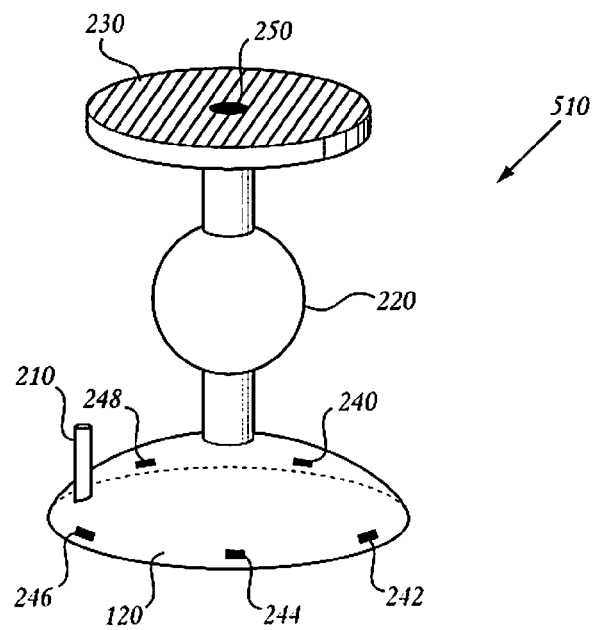
FIGS. 5A-5B depict perspective views of the contact device without the control arm attached (FIG. 5A) and with the control arm attached (FIG. 5B) in accordance with preferred embodiments of the invention.
Figure 5B:
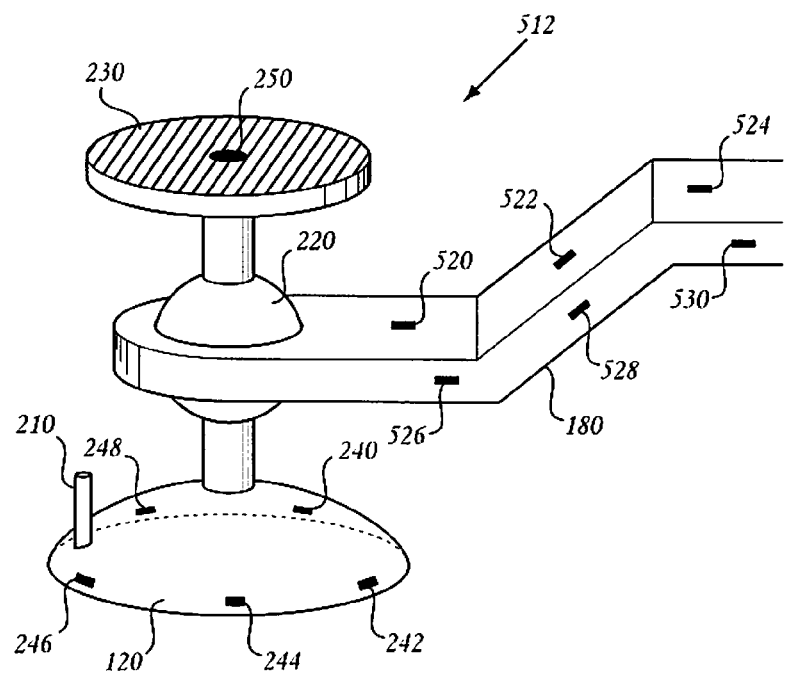

FIGS. 5A-5B are perspective and enlarged views of contact device 110 showing a preferred embodiment of the contact device 110 including the contact member 120, spherical pivot 220, mirror 230 and vacuum port 210. In this embodiment of the invention, the contact device 110 includes one or more fiducial markers 240, 242, 244, 246, 248 which define the geometry of the contact device 110 or geometric relationships between the contact device 110 and additional components of the system and/or eye as described throughout the specification. The fiducial markers, in one embodiment of the invention, contribute to the positional knowledge of the eye when the contact device 110 is engaged with the eye 130, and a coordinate system is known. Spatial registration can be used record and monitor the three dimensional spatial position of the contact device 110 relative to a known reference point.

In the embodiment illustrated in FIGS. 5A-5B, one or more of the fiducial markers 240, 242, 244, 246, 248 includes an imageable fiducial locator. The fiducial locator is locatable using one or more imaging system modalities. In this embodiment, the fiducial is capable of being mounted in or on the eye-contact member 120, such as being either flush to, or recessed from, an outer surface of eye-contact member 120. However, in alternative embodiments, the fiducial need not be configured for mounting flush to or recessed from contact member 120, and can be mounted to extend from eye-contact member 120. In another embodiment, one or more fiducials are positioned on, within, or on the perimeter of mirror 230. This allows the mirror 230, along with contact device 110, to be centered or aligned with respect to the limbus or other ocular structure.

The fiducial may include a liquid or gel housed in a sealed interior cavity. Preferably, the fiducial is a solid. The solid, gel, or fluid may be visible by one or more imaging modalities (e.g., MR, CT, etc.). In one embodiment, the fiducial is integrated into the eye-contact member itself. The imaging fiducial is visible and provides good contrast on images produced by at least one imaging modality. In one embodiment, the imaging fiducial is multimodal (i.e., locatable by more than one imaging modality), such as by using a mixture of different imaging fluids, gels or solids that are locatable on different imaging modalities.

In one embodiment, the one or more of the fiducial markers 240, 242, 244 includes a substance that is viewable on a first imaging modality, while one or more of the fiducial markers 246, 248 includes a substance that is viewable on a different second imaging modality. In one such illustrative embodiment, the one or more of the fiducial markers 240, 242, 244 includes, or is doped with, a substance having a high atomic number (Z), such as barium, titanium, iodine, gold, silver, platinum, stainless steel, titanium dioxide, etc. that provides good contrast on a CT or other radiographic imaging system. In this embodiment, one or more of the fiducial markers 246, 248 include gadopentatate dimeglumine, gadoteridol, ferric chloride, copper sulfate, or any other suitable MRI contrast agent, such as described in chapter 14 of Magnetic Resonance Imaging, 2nd ed., edited by Stark and Bradley, 1992, which is incorporated herein by reference.

In an alternative multimodal embodiment, the fiducial marker is constructed of a substantially solid plastic or other material that is hygroscopic, i.e., capable of receiving and retaining a fluid, such as an imaging fluid that is viewable on an imaging system (e.g., an MRI imaging system or the like). In a further embodiment, the plastic forming the fiducial marker is doped or otherwise includes a substance that is viewable on a different imaging system, such as, for example, a CT or other radiographic imaging system. Illustrative examples of solid plastics that can be made hygroscopic include, among other things, nylon and polyurethane. Using a hygroscopic material avoids the complexity and cost associated with manufacturing a sealed cavity for retaining an imaging fluid. Moreover, by adapting the solid hygroscopic plastic for imaging using a first modality, and by using the imaging fluid for imaging using a second modality, each of the solid and the fluid can be separately tailored toward providing better contrast for its particular imaging modality.

In a further embodiment of the fiducial markers illustrated in FIGS. 5A-5B, the outer surface of one or more of the fiducial markers is reflective of light or other electromagnetic energy. Consequently, it is locatable by a camera in an optical positioning system that is coupled to an image-guided workstation (e.g., during subject registration). One additional function of such fiducials is measurement calibration where the distance between fiducials is used to calibrate distance on or within the eye. In one such example, the outer surface of the imaging spherical fiducial marker includes light-reflective microspheres (e.g., embedded in an adhesive covering the fiducial or eye-contact member 120). In another such example, the outer surface of the fiducial is covered with an adhesive-backed light-reflective tape, such as SCOTCHLITE 9810 Reflective Material Multipurpose Tape sold by Minnesota Mining and Manufacturing Co. ("3M"), of Saint Paul, Minn.

In one embodiment of the invention, the spherical pivot 220, mirror 230 and/or the control arm 180 includes one or more fiducial markers. In an alternative embodiment of the invention, the one or more fiducial markers are configured to be locatable by a remote positioning system as well as imagable using one or more imaging modalities. In one such embodiment, the outer surface of the eye-contact member is configured to be light reflective, such as discussed above. The fiducial markers are still advantageously locatable using one or more imaging modalities (e.g., MR, CT, or other imaging system providing 3D or other internal images within a subject) as well as also being locatable external to the subject, such as by using a remote camera or like component of an optical or other positioning system, e.g., that is coupled to an image-guided workstation. In one embodiment, this permits automatic registration of the actual location of the subject's eye (e.g., using cameras to locate the light reflective fiducial markers) to pretreatment images of the system on which additional imageable fiducial markers are positioned. This eliminates the need to register the eye of the subject by inserting an optically-locatable positioning control arm onto the contact device, and eliminates the need for other absolute position reference, because the fiducial markers themselves are optically locatable and registerable to known locations on pretreatment images of the system.

FIG. 5B illustrates one embodiment of the control arm 180 coupled to contact device 110. Control arm 180 is coupled to an image-guided workstation or platform (not shown). In this embodiment, control arm 180 includes an end that is sized and shaped to permit being coupled to spherical pivot 220. The control arm 180 includes, in this embodiment, a plurality of fiducial markers 520, 522, 524, 526, 528, 530 that are locatable by a camera or other like device of the optical positioning system. The fiducial markers 520, 522, 524, 526, 528, 530 on the control arm 180 are positioned in a known spatial relationship to each other and to the tip of the control arm 180. By recognizing the locations of the fiducial markers, the optical positioning system is capable of computing the location of the control arm tip, which is in a known spatial relationship with the configuration of the fiducial markers. This permits the control arm 180 to be used in conjunction with the optical positioning system to register the eye of the subject and to further plan and/or perform the treatment procedure using an image-guided workstation. An image guided treatment computer workstation, which is capable of displaying previously acquired and loaded pretreatment images of a the system. The optical positioning system connected to the workstation includes an infrared light (or other energy source) that provides light that is reflected from the reflective fiducial markers. This permits the reflective fiducial markers on the control arm 180 to be located and recognized by the cameras.

As seen in FIGS. 5A-5B, an additional component of the contact device 110, in some embodiments and as discussed with reference to FIGS. 4B-4D above, is a lumen 250 which traverses the contact device 110 and, in some embodiments, extends to the surface of the eye. The lumen 250 can be used to pass one or more probes such as may be used to determine the axial length of the eye (e.g., an A-scan). In some embodiments, the probe includes a laser pointer probe (not shown), which can point outward away from the eye of the subject. The outward pointing laser pointer can be used to determine alignment of the device, and therefore the eye, relative to a treatment device included within the system. In some embodiments, the laser pointer is used to align the treatment device with an axis of the eye and can be used to turn the treatment device on (when in position) or off (when not in position). In these embodiments, the subject turns the device on and off, and the treatment device operates when the eye is aligned with the machine and turns off when the device is not aligned with the radiotherapy device.

In some embodiments, the contact device 110 can include material that is radiotranslucent, or that permits at least some radiation to pass. In some embodiments, the radiotranslucent material of the contact device 110 can be configured to permit the passage of therapeutic radiation beams during treatment. For example, the contact device 110 can engage the eye to maintain position of the eye, and x-ray beams can be directed to target eye tissue with a trajectory that passes through at least a portion of the contact device 110. Accordingly, a treatment planning system can plan x-ray beam trajectories without significant consideration of where the contact device 110 engages or is positioned on the eye.

In some embodiments, the contact device 110 can include both material that is radiopaque and material that is radiotranslucent. In some embodiments, the radiopaque material of the contact device 110 can be configured to limit transmission through the material of radiation, such as, for example, x-ray beams, and the radiotranslucent material can be configured to permit transmission of radiation (e.g., x-ray beams) to pass through the material. The contact device 110 can further be configured to provide alignment trajectories along which the x-ray beams will pass to the target tissue. In some embodiments, the contact device 110 can further operate as a tertiary collimator by limiting the beam size or shape. For example, the radiotranslucent material of the contact device 110 can be sized and shaped as the aperture through the secondary collimator. In such embodiments, when the x-ray beam is emitted through the radiotranslucent material, any penumbra at the contact device 110 can be blocked by the surrounding radiopaque material. In some embodiments, apertures in the radiopaque material may be provided instead of radiotranslucent materials. Accordingly, the contact device 110 can further provide shielding or targeting functions.

In some embodiments, the contact device 110 can have a radiopaque material that comprises substantially a central portion of the contact device 110 (e.g., a portion of the eye-contact member 120), and a portion of the contact device 110 extending around a periphery, or the edges, of the central portion comprises radiotranslucent material. Accordingly, the central portion can operate as a shield to structures of the eye, and the x-ray beams can pass through the radiotranslucent material during radiotherapy. Thus, the contact device 110 can have a larger eye-contact member 120 to engage the eye while still permitting x-ray beams to reach the target tissues substantially unimpeded by the radiopaque material.

FIGS. 6A-6C illustrate perspective views of the contact device 110 attached to control arm 180 which is being fed into slot 610 of drive mechanism 600. In some embodiments, the contact device 110 of the system can be attached to a coupling component to hold the eye in place. The coupling component can be attached to the treatment device, but preferably, as shown in FIGS. 6A-6C, it is attached at a location separate from the radiotherapy device, such as a drive mechanism 600 that is attached to a table or platform 620 which holds the treatment device. Contact device 110 is preferably disposable such that a separate (e.g. disposable) contact device 110 is employed for each subject and/or use. Alternatively, contact device 110 may be nondisposable and be treated, e.g., with anti-infective agents, prior to being utilized in multiple subjects' eyes. Drive mechanism 600 is fixed to base 620 through connector 640, which is may robotically controlled, but preferably manually controlled, and has a known coordinate system. In one embodiment, drive mechanism 600 is fixed in a known, or predetermined, location with respect to the head positioning system (not shown) and/or the eye of the subject (not shown) and/or the positioning system of the radiotherapy device. Push button 630 allows free manual positioning of contact device 110 into and/or out of slot 610. Thus, as illustrated in FIG. 6A, the control arm 180 is not engaged with the drive mechanism 600. In FIG. 6B, the control arm 180 is partially engaged with the drive mechanism 600. And in FIG. 6C, the control arm 180 is fully engaged with the drive mechanism 600 and is fixed in a known, or predetermined location, which allows the eye of the subject to be fixed in a known, or predetermined location, when contact device 110 engages the eye.

In one embodiment of the invention, spatial registration is used in combination with the system to record and monitor the three dimensional spatial position of the contact device 110 at all times, relative to a known reference point. One method of accomplishing the registration is through the use of a spatially encoded control arm 180, which tracks the position of the contact device 110. The control arm 180 holds the contact device 110 at one end, and is mechanically stabilized or fixed to the platform 620 at the other end. The control arm 180 engages drive mechanism 600, allowing at one degree of freedom and up to three or more degrees of freedom, and may employ encoding devices to accurately determine the position and orientation of the contact device 110 relative to the platform. The control arm 180 also allows movement and positioning of the contact device 110. The control arm 180 is used to accurately and reproducibly position the contact device 110 The positional information of the contact device 110 is then conveyed to localization software for registration of the position of the eye.

Another method to accomplish the spatial registration and guidance of the contact device 110 is through optical or electromagnetic sensor detection. In this technique, cameras or other concentrated detectors are mounted either on the system, or optionally in the treatment room, and are used to track and register the position of the eye or contact device 110. Cameras or detectors are then able to determine and record the three dimensional position of the contact device 110 in real time, and therefore the position of the eye as it is positioned. A calibration process can be used to determine the relative spatial position of the contact device to a known reference frame, as well as in combination with optional images. The calibration information can be stored in a reference file on the computer and used by a software program.

FIGS. 7A-7C illustrate a preferred eye stabilizing and positioning embodiment of the invention. In FIG. 7A, contact device 110 is moved toward eye 130 along directional arrows 710, 712 such that eye-contact member 120 contacts eye 130. A vacuum is applied through vacuum port 210 to remove substantially all air trapped between eye-contact member 120 and eye 130, such that contact device 110 is sealingly engaged with eye 130. FIG. 7B illustrates the positioned and stabilized eye 130. FIG. 7C shows downward, or Y-directional movement of control arm 180 of contact device 110. In a preferred embodiment, movement of control arm 180 is performed by a trained medical professional. Upon directional displacement (e.g. X-Y control of arm 180), control arm 180 pivots about spherical pivot 220 such that eye 130 is controllably moved and/or positioned. In one embodiment of the invention, sensor feedback provides the location of the eye 130. In another embodiment, control arm 180 is connected to a drive mechanism, as illustrated in FIGS. 6A-6C, which allows automated control and position information of the eye 130 as it is moved or positioned.

With continuing reference to FIGS. 7A-7C, an exemplary method of utilizing the system of the invention includes rotating the eye prior to application of treatment. The eye can be gripped and rotated an amount, such as, for example about 1 to 2 degrees, or more broadly about 1 to 90 degrees, about the center point. In other implementations, the rotation may range from about 1 to about 45 degrees or more, and/or at different points in time, in different directions and/or in different amounts. Following such rotation, the eye may, or may not, be held in the rotated position, for example while some or all of the treatment(s) are applied. After application of some or all of the desired treatment, the eye can be moved back, to a full or partial extent, to its naturally-occurring orientation and/or can be released such that the eye moves, to a full or partial extent, back to its naturally-occurring orientation without assistance from the system.

In some embodiments of the invention, after application of some or all of the desired eye treatment(s), the eye can be rotated in the opposite direction to a greater extent than that to which it was first rotated, such as rotation in the counterclockwise direction about 1 to 90 degrees. Following any of the rotations of the eye described herein, and/or at any intermediate step, part or all of the eye being rotated and/or treated may be held (temporarily or permanently) by means in addition to the contact device 110 illustrated in FIGS. 7A-7C.

In other embodiments of the invention, following an initial stabilization and rotation, or positioning, of the eye, and application of one or more treatments to the eye (e.g., radiotherapy), the eye can be rotated in the same direction to a greater extent than to which it was first rotated. Then, one or more desired eye treatments can again be administered. The process can be repeated to form additional eye treatments to, for example, focus energy on a single spot, e.g., the macula, such that the sclera is minimally impacted. The eye can be rotated in the opposite direction (e.g., past the original, naturally occurring orientation) to various degrees to facilitate administration of one or more tissue treatments. Accordingly, the eye can be rotated in both directions to facilitate administration of treatment such that potential scleral damage and/or healing time can be attenuated or eliminated.

In one embodiment of the invention, the system includes a fluid dispenser. Fluids, including water, sterile water or conditioned fluids, such as those described in U.S. Pat. Nos. 5,785,521 and 6,350,123, the contents of which are incorporated herein by reference, may be added to assist with healing times or otherwise aid the treated tissue. For example, fluid may be applied by way of a small air mister, e.g., from a local or remotely disposed reservoir or dropper, affixed to the system. The fluid may be applied between and/or during application of treatment, to attenuate or eliminate charring and/or wash away blood. Alternatively, fluid may be applied using a sprayer line affixed to the treatment device, contact device or otherwise affixed on the system. The sprayer line may include tubing, e.g., clip-on and/or silicone based tubing, built into the system and a fluid dispensing unit. The fluid-dispensing input may be activated manually or automatically to power dispensation of fluid.

FIGS. 7A-7C also illustrate the application of a biasing force 155 by arm 180 during an eye-positioning procedure. As noted above, this force is used to hold the eye-contact member on the eye, such that the negative pressure between the eye and eye-contact member can function to stabilize the position of the eye, but at a relatively low vacuum. In this embodiment of the invention, an eye-contact assembly, indicated at 117, includes an eye-contact member 120 and a biasing mechanism for biasing the eye-contact member against the patient's eye with a force of between 1-25 grams. In the embodiment illustrated, the biasing mechanism is contained within arm 120, and indicated by direction-of-force arrow 119. As noted above, the biasing mechanism may take the form of a coiled spring or circuit-activated solenoid that biases the arm in the direction of arrow 119.

In another embodiment of the system, the eye-contact member may be supported on a track for sliding movement toward and away from the eye, along an axis substantially normal to the axis of the eye, where the track may be mounted, for example, on the head support for positioning in up-and-down and left-and-right directions, to place the track immediately in front of the patients eye. With this positioning the eye-contact member can then be moved top engage the front of the patient's eye, with the patient looking straight ahead. Once initial contact is made, and after removing air from the eye/contact member interface, a biasing force can be applied to the contact member to hold to against the eye during a subsequent eye therapy procedure.

FIGS. 8A and 8B depict a mechanism by which the contact device 110 can be used to align the eye with laser alignment system 800. Optionally, the alignment mechanism also directly aligns a treatment system, such as a radiotherapy system (not shown) in which the radiotherapy system directs its energy toward the eye in relation to the alignment system. Laser pointer beam 810 (which is collinear with the therapeutic beam in some embodiments) is emitted from laser system 800 through a collimator opening 820 and reflects off the surface of mirror 230 of the contact device 110. In the non-alignment case depicted in FIG. 8A, the laser pointer beam 810 will not reflect off the surface of mirror 230 collinearly with the collimator opening 820, but will be off-axis, as shown by reflection beam 830. The orientation of the laser system 800 and/or the contact device 600 can be manually or automatically adjusted by direct visualization of the location of the reflection beam 830 or by sensors that detect the location of the reflection beam 830 and adjust the laser system 800 to bring the laser reflection beam 830 into alignment. In the case where the laser pointer is in fact aligned (FIG. 8B), the laser pointer beam 810 is reflected, and the laser reflection beam 830 is substantially collinear with the laser pointer beam 830. The system includes, in some embodiments, a sensing module that senses a position of the eye and relays information concerning the position of the eye to the position guide. The sensing module can include a portion that physically contacts the eye, which can include the eye-contact member 120 positionable on or over the cornea of the eye. The sensing module can, in some embodiments, optically sense the position of the eye with, for example, a laser.

Some embodiments of the invention, as shown in FIGS. 9-24, provide that the eye-contact member have one or more apertures or portions of radiotranslucent material positioned radially around a center of the eye-contact member 120. The apertures can be shaped as circles, squares, rectangles, ovals, curvilinear, irregular, annular, concentric rings, and so forth. In some embodiments, the contact device 110 is configured to include an aperture or portion of radiotranslucent material only in a center portion of the device to permit transmission of radiation therethrough to target tissue.

Figure 9:
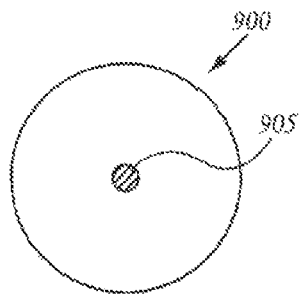
FIG. 9 is a frontal plan view of an embodiment of an eye-contact member with no aperture included within the eye-contact member.
Figure 10:
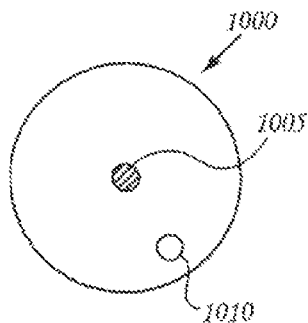
FIG. 10 is a frontal plan view of an embodiment of an eye-contact member with a circular shaped aperture offset from the center of the eye-contact member.

FIGS. 9-24 illustrate a variety of embodiments of eye-contact members that can be used to selectively control the therapeutic energy (e.g., radiotherapy) emitted through the eye-contact members toward the eye. FIG. 9 shows one embodiment of the eye-contact member 900. As seen, the eye-contact member 900 includes a connector 905 for coupling the eye-contact member 900 to a control arm (not shown) as discussed above. The eye-contact member 900 is positioned onto an exterior surface of the eye. There is no aperture or opening located on the eye-contact member 900 as shown in FIG. 9. FIG. 10 illustrates a circular aperture 1010 located off center of eye-contact member 1000, which can be coupled to a control arm through connector 1005. The circular aperture is preferably transmissive of energy to the eye of a subject when used in combination with a therapeutic treatment device, such as a radiotherapy device allowing precise control of energy through the eye onto a predetermined structure located within the eye, e.g., the macula. The diameter of the apertures can be of any range suitable for the treatment selected. In particular embodiments of the invention, the diameter of the aperture ranges from about 25 microns to about 200 microns. A 100 micron aperture is contemplated in one embodiment. In an alternative embodiment, a 200 micron diameter aperture is utilized.

Figure 11:
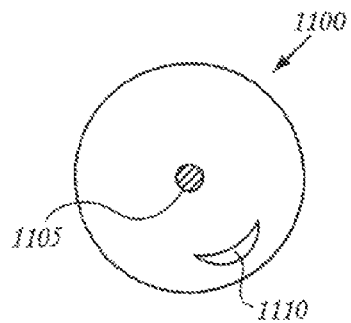
FIG. 11 is a frontal plan view of an embodiment of an eye-contact member with an irregular shaped aperture offset from the center of the eye-contact member.
Figure 12:
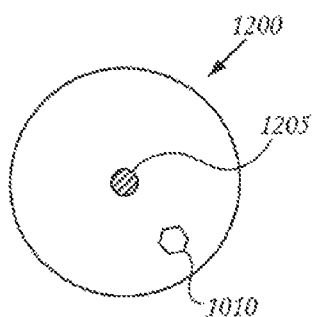
FIG. 12 is a frontal plan view of an embodiment of an eye-contact member with an heptagonal shaped aperture offset from the center of the eye-contact member.
Figure 13:
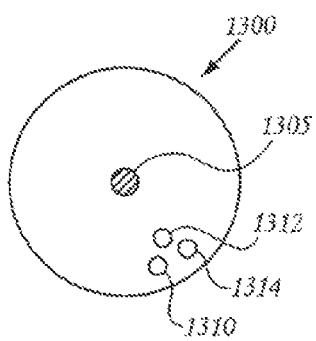
FIG. 13 is a frontal plan view of an embodiment of an eye-contact member with a plurality of circular shaped apertures offset from the center of the eye-contact member.
Figure 14:
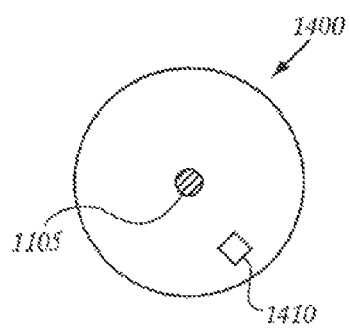
FIG. 14 is a frontal plan view of an embodiment of an eye-contact member with a diamond shaped aperture offset from the center of the eye-contact member.
Figure 15:
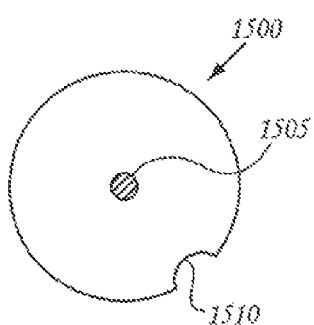
FIG. 15 is a frontal plan view of an embodiment of an eye-contact member with a circular shaped aperture offset from the center, and located at the edge, of the eye-contact member.
Figure 16:
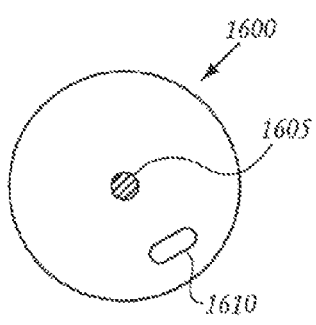
FIG. 16 is a frontal plan view of an embodiment of an eye-contact member with a kidney shaped aperture offset from the center of the eye-contact member.
Figure 17:
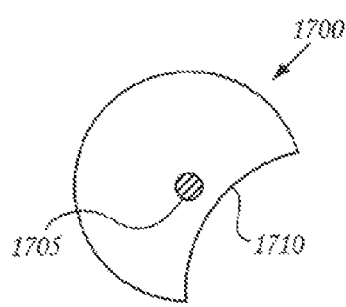
FIG. 17 is a frontal plan view of an embodiment of an eye-contact member with a circular shaped aperture offset from the center, and located at the edge, of the eye-contact member.
Figure 18A:
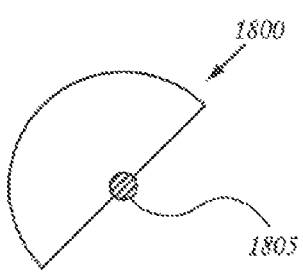
FIGS. 18A-B are frontal plan views of embodiments of an eye-contact member with up to one half of the eye-contact member removed (FIG. 18A), and more than one half of the eye-contact member removed (FIG. 18B)
Figure 18B:
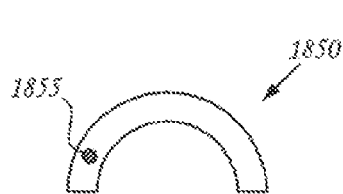

FIGS. 11-18 are similar to the eye-contact member 1000, except as set forth below. Accordingly, the eye-contact members described in connection with FIGS. 11-18 can be used and applied to the eye of a subject in a similar fashion to the eye-contact members 900 or 1000. For example, FIG. 11 shows an embodiment of an eye-contact member 1100 that includes a connector 1105 and an aperture 1110 formed in the shape of a crescent. FIG. 12 shows another embodiment of an eye-contact member 1200 that includes a connector 1205 and an aperture 1210 formed in the shape of a heptagon. FIG. 13 shows another embodiment of an eye-contact member 1300 that includes a connector 1305 and a plurality of apertures 1310, 1312, 1314 formed in the shape of circles. FIG. 14 shows another embodiment of an eye-contact member 1400 that includes a connector 1405 and an aperture 1410 formed in the shape of a diamond. FIG. 15 shows another embodiment of an eye-contact member 1500 that includes a connector 1505 and an aperture 1510 formed in the shape of a partial circle located at the periphery of eye-contact member 1500. FIG. 16 shows another embodiment of an eye-contact member 1600 that includes a connector 1605 and an aperture 1610 formed in the shape of a kidney. It will be appreciated that the apertures shown in FIGS. 11-12, 14, 16 and 18 are merely exemplary of non-circular apertures. Other shapes and arrangements may also be provided and are within the scope of the present invention. FIG. 17 shows another embodiment of an eye-contact member 1700 that includes a connector 1705 and an aperture 1710 formed in the shape of a partial circle formed at the periphery of eye-contact member 1700. FIG. 18 shows another embodiment of an eye-contact member 1800 that includes a connector 1805 and an overall shape that covers approximately half the area of an eye relative to the eye-contact member 900 of FIG. 9. Thus, the eye-contact member 1800 may allow more treatment energy and/or easier access to the eye.

The eye-contact members of FIGS. 9-18 preferably have a constant thickness. However, in some embodiments, the thickness of the eye-contact members may vary between the outer periphery and the center of the eye-contact members. For example, the thickness of the eye-contact member may gradually decrease from the center to the periphery of the eye-contact member to allow more energy to enter the eye at the periphery than enters nearer the center. The eye-contact members are, in some embodiments at least partially and preferably completely opaque, outside the one or more aperture regions. The opacity of the eye-contact members may be achieved in any of several different ways. For example, in one embodiment, the material used to form the eye-contact member may be naturally opaque. Alternatively, the material used to form the eye-contact member may be substantially clear, but treated with a dye or other pigmentation agent to render a portion or all of the eye-contact member substantially or entirely opaque. In still another embodiment, one or both of the surfaces of the eye-contact members may be treated physically or chemically (such as by etching) to alter the refractive and transmissive properties of the eye-contact member making it less transmissive of energy.

In still another alternative, the surface of the eye-contact member may be treated with a particulate deposited thereon. For example, the surface of the eye-contact member may be deposited with particulate of titanium, gold or carbon to provide opacity to the surface of the eye-contact member. Radiopaque materials such as barium or florescent compounds can also be included. In another alternative, the particulate may be encapsulated within the interior of the eye-contact member. Finally, the eye-contact member may be patterned to provide areas of varying energy transmissivity, as generally shown in FIGS. 19-24, which are discussed in detail below.

FIG. 19 shows an embodiment of an eye-contact member 1900 that includes a connector 1905 and a plurality of apertures 1910 in the pattern of radial spokes extending from the connector 1905 to an outer periphery of the eye-contact member 1900. The apertures may have the same opacity, or alternatively have opacities that gradually increase or decrease, as desired. The graduated opacity may be achieved by, for example, providing different degrees of pigmentation to the apertures 1910. In another embodiment, energy blocking materials of the type described above in variable degrees may be selectively deposited on the surface of the eye-contact member 1900. FIG. 20 is a side view of the eye-contact member of FIG. 19 showing a plurality of radially extending slots 1910 emanating from the center 1905 of the eye-contact member.

In a similar manner, FIG. 21 shows an embodiment of an eye-contact member 2100 that includes a connector 2105 and a plurality of circular apertures 2110, 2112 and 2114 that increase in diameter from the center to the periphery of eye-contact member 2100. FIG. 22 is a side view of the eye-contact member of FIG. 21 showing a plurality of circular shaped apertures 2110, 2112, 2214 increasing in size and radially spaced from the center 2205 of the eye-contact member 2200.

FIG. 23 illustrates an embodiment of an eye-contact member 2305 which utilizes a patterned aperture structure which includes areas ranging that are opaque 2320 to areas that are transmissive of energy 2310. FIG. 24 is a side view of the eye-contact member of FIG. 23 showing a grid of apertures 2310 within the eye-contact member 2300.

In the embodiments described above, the selected treatment device is indirectly coupled to the contact device through attachments to the system. For example, in a preferred embodiment described above, the contact device is coupled to a control arm which is connected to the system through a drive mechanism; and the selected treatment device is coupled to the system such that the spatial relationship between the contact device and the selected treatment device can be dynamically determined. In an alternative embodiment of the present invention, there exists a direct physical connection between the contact device and the selected treatment system. Thus, in some embodiments, the physical connection can include a treatment coupling device. The coupling device has an eye-contact member which can include, for example, a scleral lens and a treatment device coupling surface. The eye-contact member can cover the cornea and contact the cornea or it can cover the cornea, only contacting the sclera. In some embodiments, the eye-contact member can cover and contact both the cornea and the sclera. The eye-contact member can be a lens in some embodiments, and in alternative embodiments, the eye-contact member can be a substantially transparent window with little or no refraction. The eye-contact member can be used to retain ocular gel or it can be shell with a hole in the center. The eye-contact member can be customized for an individual patient using imaging modalities, such as for example, an IOL master, optical coherence tomography (OCT), corneal surface mapping, MRI, CT scan, and ultrasound. The eye-contact member can be flexible or rigid or a composite. One or more flanges can function to hold the eyelids apart or can serve as a fiducial for the treatment device.

Opposite the eye-contact member are treatment device coupling surfaces, or portions. These surfaces, individually or collectively, couple the coupling device with the radiotherapy system. While the eye-contact member interfaces with the eye and structures, the treatment portion couples the eye-contact member to the treatment system. The treatment portion can link the coupling device to the treatment device in a variety of ways. For example, the treatment portion can couple to the treatment device via laser pointer, via infrared coupling, via microwave coupling, via mechanical coupling, via reflection, or via radiofrequency transmitters.

III. Methods of the Invention

Figure 25:
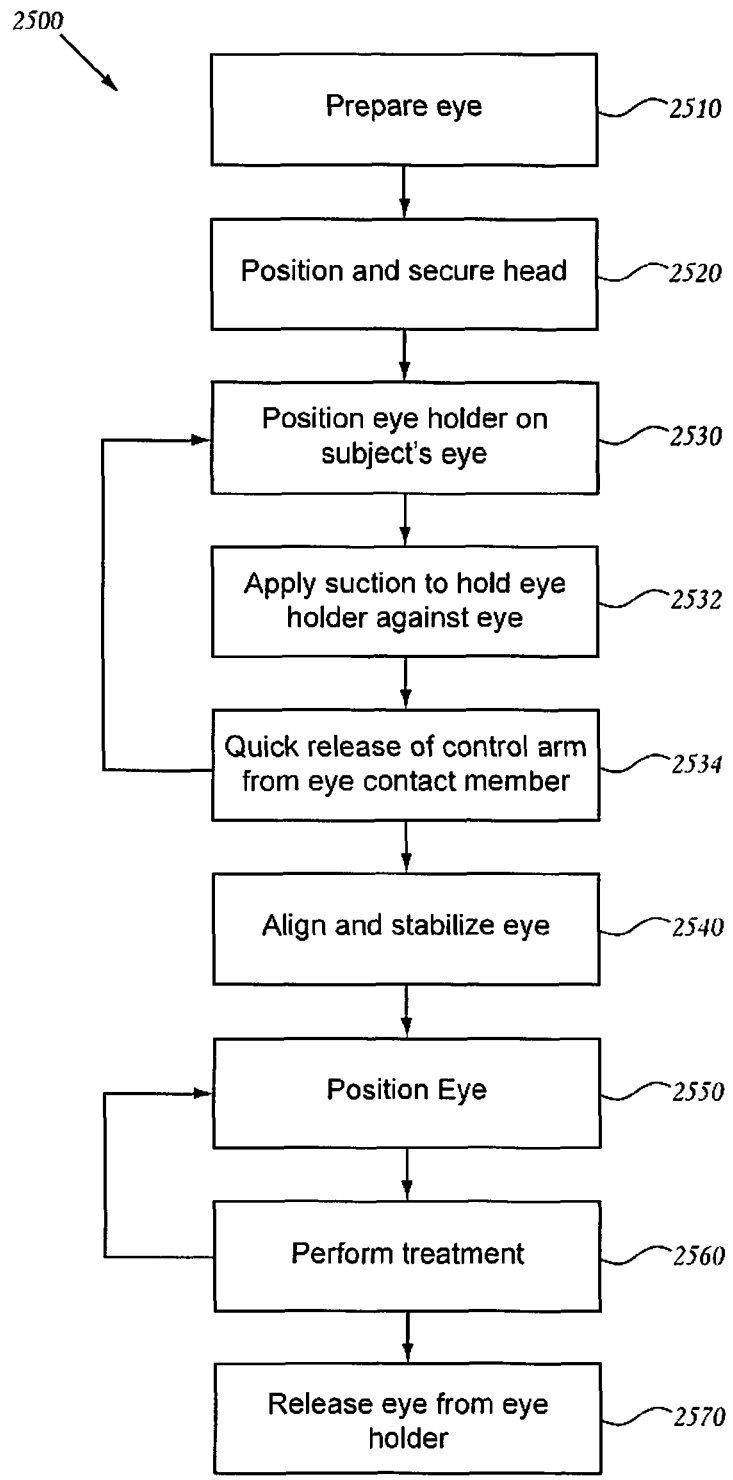
FIG. 25 is a flow chart illustrating one method of utilizing the system for stabilizing and positioning an eye for treatment.

The device of the present invention may be used in a wide variety of ocular treatment methods. Preferred treatment methods include laser therapy and radiation therapy. As illustrated in FIG. 25, a preferred method 2500 of employing the system described above includes preparing a subject's eye for treatment 2510 which can include delivering an anesthetic, taping the upper or lower lid, dilating the eye, measuring biometric parameters such as axial length, corneal diameter, etc. Following preparation, the subject's head is secured to the system 2520. The contact device is then positioned on the subject's eye as referenced by reference numeral 2530. Positioning of the holder (described above) on the eye is accomplished by aligning the center of the holder, using the x,y,z movement, with the center of the limbus. This can be performed as an approximation by a physician while observing the both the holder and the eye of the patient directly or on a computer monitor. Alternatively, an imaging camera can determine the center of the limbus automatically and aid in the positioning of the holder with its center aligned with the center of the limbus. In some embodiments, the holder is positioned in place automatically rather than manually by the device operator.

Once the position of the holder relative to the limbus is determined, suction is applied through the holder to appose it to the eye 2532. With the holder firmly attached to the eye, the holder (and eye) can be moved into position relative to the treatment device in known coordinates within the system. In the embodiment where the holder contains a mirror to monitor its reflection, the holder is positioned such that a reflection from the mirror is in position. Once the eye is in position, its movement is stabilized 2540 with suction in one example. The eye can then be positioned to a predetermined location relative to the treatment device, as indicated by numeral 2550. The treatment device is then moved about, or otherwise positioned relative to, the eye to deliver its treatment 2560. Alternatively, the treatment device moves into position about the eye. Method steps 2550-2560 can be repeated until a desired treatment is completed, after which the subject's eye is released from the contact device 2570.

As described above and indicated by numeral 2534, a quick release is built into the contact device in some embodiments of the invention. In case of an emergency or fatigue, the patient can release from the holder by a applying a modicum of force which results in the eye-contact member breaking away from the remainder of the contact device. In such a case, the method step returns to the step prior to positioning and securing the head 2520, or to the step of positioning the contact device on the subject's eye 2530, as indicated in FIG. 25.

An exemplary method for utilizing the system is now described. The method includes preparing the eye for positioning. Such preparation includes applying eye numbing drops to the eye of the subject. Scleral clearance can be provided by securing the lower eyelid downward with tape or eyelid eversion. The untreated eye is covered with a patch. The subject's head is positioned in a head support and the chin is rested on a chinrest. The head may be secured to the head support with straps or the like. The eye-contact member is placed on the cornea by tilting the eye-contact member to contact the upper portion of the sclera. As the eye-contact member contacts the upper scleral region of the eye, the eye-contact member is tilted downward to achieve full contact with the eye. Suction is then applied, and verified visually and by the vacuum source which "holds" suction. The contact device is then aligned with a laser, and centered on the limbus. A desired treatment procedure is then performed.

Figure 26:
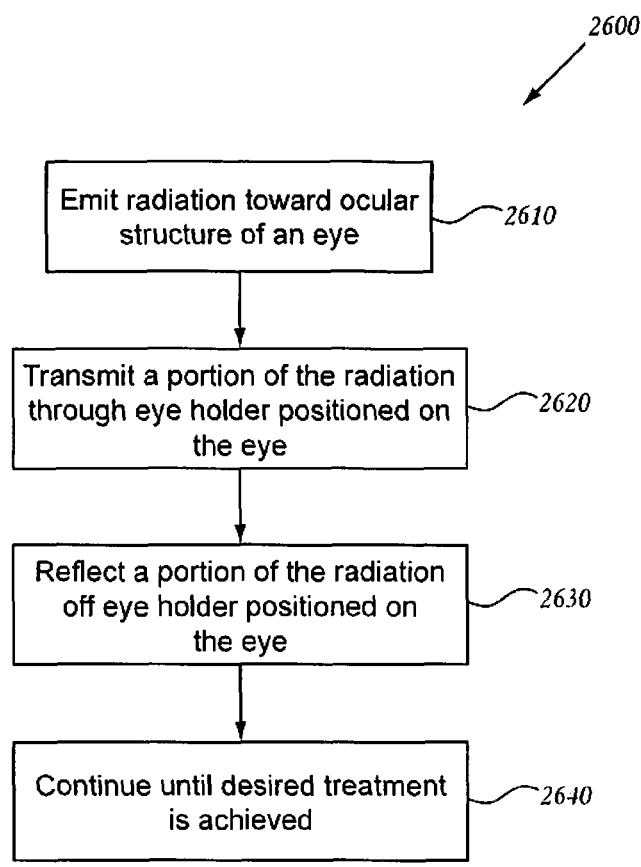
FIG. 26 is a flow chart illustrating a method of utilizing the system for treating an eye with radiation in accordance with one embodiment of the invention.

In a preferred embodiment of the method of the invention as illustrated in FIG. 26, a method 2600 of treating an ocular structure of an eye with a radiation beam from a radiotherapy system is described, including contacting a surface of the eye with an eye-contact member, wherein the eye-contact member comprises a first portion, such that an axis passing through the ocular structure also passes through the first portion of the eye-contact member; and emitting a plurality of radiation beams toward the ocular structure 2610, from a radiotherapy system located outside the eye, such that the plurality of radiation beams each have a trajectory that intersects the axis at a treatment site at the ocular structure, the treatment site being effectively treatable by at least one of the plurality of radiation beams. In the embodiment illustrated in FIG. 2600, at least a portion of the radiation is transmitted through the contact device which has been positioned on the eye. In an alternative embodiment, at least a portion of the radiation is transmitted to the eye without contacting any portion of the contact device. In yet another embodiment, which can be used as an alternative or in combination with the embodiments described above, at least a portion of the radiation is reflected off the contact device when the contact device is positioned on the eye 2630. The radiation treatment is continued until a desired effect is achieved 2640.

Figure 27:
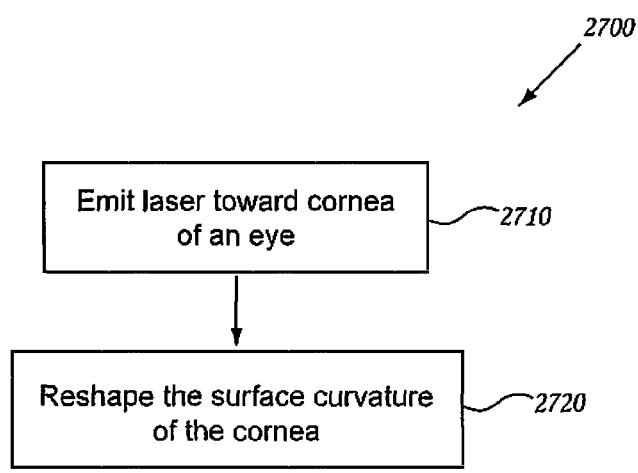
FIG. 27 is a flow chart illustrating a method of utilizing the system for laser treating an eye in accordance with another embodiment of the invention.

In another embodiment of a method of the invention 2700, as illustrated in FIG. 27, the cornea is reshaped using the system of the invention described above. In this embodiment, a laser is emitted toward the cornea of an eye 2710, followed by the desired reshaping of the surface of the cornea 2720. According to some embodiments of the invention, applying treatment energy (e.g., radiotherapy or ablating optical energy) to tissues (e.g., the conjunctiva or sclera) can refer to tissue treatment groupings and/or tissue treatment markings corresponding to tissue treatment groupings. Treatment can refer to two or more tissue treatments arranged in a focused spot or spots on the tissue; a nonlinear and nonarcuate grouping (e.g., pattern) on the tissue; and/or arranged in a plurality of focused spots, nonlinear and nonarcuate groupings on the tissue. Tissue treatments or groupings of tissue treatments may include focused spots, random line shapes, (straight, curved, or otherwise), or may include line shapes formed in a pattern that is predetermined based on a treatment customized to a tissue area.

In another embodiment, the system described above is used to stabilize an eye during laser photocoagulation of the retina or during a photodynamic treatment of the retina. In these treatments, stabilization of the eye is currently performed by the physician who holds the eye manually with a lens contacting the eye. A limitation of this technique is that the physician can only hold the lens with very limited positioning and stabilization ability subject to tremor and shake. Given the system above, the physician would be able to apply these treatments with confirmation of stability through the system camera stabilizing arm.

Particular implementations of lasers for use on, for example, the sclera may include Er:YAG, Er:YSGG, Er, CTE:YAG, or Cr:YSGG lasers operated at exemplary wavelengths ranging from about 2.7 to 2.9 microns; XeCl excimer lasers operated at an exemplary wavelength of about 308 nm; frequency-shifted solid state lasers operated at exemplary wavelengths of about 0.15 microns to about 3.2 microns; excimer lasers of ArF operated at a wavelength of about 93 nm; harmonic generations of Nd:YAG or Nd:YAL or Ti:sapphire lasers operated at wavelengths of about 190 nm to about 220 nm; CO lasers operated at a wavelength of, for example, about 6 microns and carbon dioxide lasers operated at a wavelength of, for example, about 10.6 microns; diode lasers operated at exemplary wavelengths of about 0.8 microns to about 2.1 microns; gas lasers operated at wavelengths of about 2.6 microns to about 3.2 microns; and other gas or solid state lasers including flash-lamp and diode-laser pumped lasers operated at wavelengths of about 0.5 microns to about 10.6 microns; and optical parametric oscillation (OPO) lasers operated at exemplary wavelengths of about 2.6 microns to about 3.2 microns.

Thus, the devices and methods described above are useful, in some embodiments of the invention, to treat conditions of the eye of a subject. Sources of treatment energy, such as electromagnetic energy emitting devices, can be utilized to implement corneal and/or non-corneal manipulations. According to the architectures and techniques of some embodiments of the invention, the source or sources (when utilized in combination) can be activated to direct energy onto and/or into parts of the eye, such as the conjunctiva and sclera to treat conditions such as presbyopia, wherein the energy affects at least one property of the eye and results in an enhancement in a property of the eye.

In some embodiments of the invention, focusing disorders such as myopia and hyperopia are treated. Myopia, or nearsightedness, relates to an eyesight refractive abnormality whereby distant objects appear blurred as a result of rays of light entering the eye being brought to focus in front of the retina. Hyperopia, or farsightedness, on the other hand, relates to an eyesight refractive abnormality whereby near objects appear blurred or fuzzy as a result of light rays being brought to focus behind the retina.

One variation of hyperopia is presbyopia, which typically is associated with a person's lack of capacity to focus at near distances and which tends to develop and progress with age. Regarding this progression, presbyopia is thought to advance as the eye progressively loses its ability to accommodate or focus sharply for near vision with increasing age of the person. Accordingly, the condition of presbyopia generally signifies a universal decrease in the amplitude of accommodation of the affected person.

Myopia and hyperopia can be treated surgically using techniques including corneal interventions, such as reshaping a surface curvature of the cornea located inside of the limbus area, and non-corneal manipulations, such as altering properties of the sclera (which is located outside of the limbus area), ciliary muscle, zonules, or lens. An example of the former treatment includes ablating the surface of the cornea itself to form a multifocal arrangement (e.g., distance vision in one eye and reading vision in another eye according to a treatment plan referred to as monovision) facilitating viewing by a patient of both near and far objects. An example of the latter treatment includes introducing kerfs into portions of the sclera to thereby increase accommodation. Non-corneal interventions typically include temporarily removing or pulling back the subject's conjunctiva, using forceps and scissors and/or one or more of scalpels, cautery, plasma, and laser methods, followed by the actual non-corneal manipulations (e.g, forming kerfs in the sclera). After completing the kerfs, the conjunctiva is then typically sutured back into position.

Electromagnetic energy devices may include, for example, lasers emitting a wide range of wavelengths, such as lasers having wavelengths ranging, for example, from about 0.2 microns to about 3.1 microns. Exemplary laser beam sizes can range from about 0.005 mm up to about 1.0 mm, or 2.0 mm. Exemplary laser energy per pulse values can range from about 0.1 mJ to about 50 mJ depending on, for example, the pulse duration and the laser beam spot size. Typical pulse laser widths may range from about 150 nanoseconds to about 1000 microseconds. The areas to be treated can be pre-traced with a vascular laser or long pulse Er, Cr:YSGG, or long pulse Er:YAG, to minimize bleeding.

In one embodiment of the invention, radiotherapy is administered. Radiotherapy is particularly useful for treating macular degeneration. Macular degeneration is a condition where the light-sensing cells of the macula, a near-center portion of the retina of the human eye, malfunction and slowly cease to work. Macular degeneration is the leading cause of central vision loss in people over the age of fifty years. Clinical and histologic evidence indicates that macular degeneration is in part caused by or results in an inflammatory process that ultimately causes destruction of the retina. The inflammatory process can result in direct destruction of the retina or destruction via formation of neovascular membranes which leak fluid and blood into the retina, quickly leading to scarring. In treating macular degeneration, the patient's macula is identified as the target region of interest. After stabilizing and positioning the eye, in accordance with the methods described above, a source of soft collimated x-rays beams is moved to a position to direct the beam at the macular region of the eye, along a path through an outer side region of the eye that makes an angle with an axis normal to the cornea of the eye between 5-45 degrees, and preferably at an angle that avoids directing the beam through the lens of the eye. In one preferred treatment method, the beam source is moved, at the same angle with respect to normal, to tilted positions in which the beam is aimed at the macula from a slightly elevated position, and from a corresponding below-elevation condition, such that the macula is irradiated along different paths, to minimize the radiation seen by the eye along any one path.

Radiotherapy can be used in combination with other therapeutics for the eye. Radiotherapy can be used to limit the side effects of other treatments or can work synergistically with other therapies. For example, radiotherapy can be applied to laser burns on the retina or to implants or surgery on the anterior region of the eye. Radiotherapy can be combined with one or more pharmaceutical, medical treatments, and/or photodynamic treatments or agents. For example, radiotherapy can be used in conjunction with anti-VEGF treatment, VEGF receptors, steroids, anti-inflammatory compounds, DNA binding molecules, oxygen radical forming therapies, oxygen carrying molecules, porphyryn molecules/therapies, gadolinium, particulate based formulations, oncologic chemotherapies, heat therapies, ultrasound therapies, and laser therapies.

In some embodiments, radiosensitizers and/or radioprotectors can be combined with treatment to decrease or increase the effects of radiotherapy, as discussed in Thomas, et al., Radiation Modifiers: Treatment Overview and Future Investigations, Hematol. Oncol. Clin. N. Am. 20 (2006) 119-139; Senan, et al., Design of Clinical Trials of Radiation Combined with Antiangiogenic Therapy, Oncologist 12 (2007) 465-477; the entirety of both of these articles are incorporated by reference herein. Some embodiments include radiotherapy with the following radiosensitizers and/or treatments: 5-fluorouracil, fluorinated pyrimidine antimetabolite, anti-S phase cytotoxin, 5-fluorouridine triphosphate, 2-deoxyfluorouridine monophosphate (Fd-UMP), and 2-deoxyfluorouridine triphosphate capecitabine, platinum analogues such as cisplatin and carboplatin, fluoropyrimidine, gemcitabine, antimetabolites, taxanes, docetaxel, topoisomerase I inhibitors, Irinotecan, cyclo-oxygenase-2 inhibitors, hypoxic cell radiosensitizers, antiangiogenic therapy, bevacizumab, recombinant monoclonal antibody, ras mediation and epidermal growth factor receptor, tumor necrosis factor vector, adenoviral vector Egr-RNF (Ad5.Egr-TNF), and hyperthermia. In some embodiments, embodiments include radiotherapy with the following radioprotectors and/or treatments: amifostine, sucralfate, cytoprotective thiol, vitamins and antioxidants, vitamin C, tocopherol-monoglucoside, pentoxifylline, alpha-tocopherol, beta-carotene, and pilocarpine.

Antiangiogenic Agents (AAs) aim to inhibit growth of new blood vessels. Bevacizumab is a humanized monoclonal antibody that acts by binding and neutralizing VEGF, which is a ligand with a central role in signaling pathways controlling blood vessel development. Findings suggest that anti-VEGF therapy has a direct antivascular effect in human tissues. In contrast, small molecule tyrosine kinase inhibitors (TKIs) prevent activation of VEGFRs, thus inhibiting downstream signaling pathways rather than binding to VEGF directly. Vascular damaging agents (VDAs) cause a rapid shutdown of established vasculature, leading to secondary tissue death. The microtubule-destabilizing agents, including combretastatins and ZD6126, and drugs related to 5,6-dimethylxanthenone-4-acetic acid (DMXAA) are two main groups of VDAs. Mixed inhibitors, including agents such as EGFR inhibitors or neutralizing agents and cytotoxic anticancer agents can also be used.

Thus, the system of the present invention can be used in some embodiments to provide radiotherapy treatment. A treatment axis which provides a reference about which application of the radiation beams are applied can be coupled to or aligned with a system axis of the radiotherapy system, about which an x-ray source can be rotated. The x-ray source can rotate about the system axis of the radiotherapy device, about which the x-ray source can be rotated. The x-ray source can rotate about the system axis with or independent from an imaging subsystem and its corresponding axis. With the treatment axis aligned with the system axis, and with the coupling device engaging the eye, trajectories of the radiation beams can be determined to direct the radiation beams to be coincident with the target tissue of the eye of the subject. The defined space of the treatment axis, the system axis, the location of the coupling device, and the location of the x-ray source provides a confined coordinate frame that can be used, for example, for directing orientation and administration of the radiation beams.

In one embodiment of the invention, radiodynamic therapy is administered. Radiodynamic agents can be administered either systemically or into the vitreous; the region in the eye to be treated is then directly targeted with radiotherapy as described above. The targeted region can be precisely localized using the device of the invention and/or in combination with an eye model, and then radiation can be precisely applied to that region. Beam sizes of about 1 mm or less can be used in radiodynamic therapy to treat ocular disorders if the target is drusen for example. In other examples, the beam size is less than about 6 mm.

It is further contemplated that the system of the present invention can be utilized to treat a variety of types of cancer of the eye. Exemplary cancer treatments are described below.

Intraocular melanoma starts from pigment cells called melanocytes, which are found in the part of the eye known as the uvea. The uvea includes the iris, which forms the colored part of the eye; the ciliary body, which helps change the shape of the lens inside the eye so that it can focus; and the choroid, which is a very deep layer of the eye. Though it is uncommon, uveal melanoma is the most common primary eye tumor in adults; approximately 1200 people are diagnosed with the disease each year in the United States. Factors associated with the disease's development include light skin color, environmental exposure and genetic predisposition.

If the melanoma begins in the iris, it may appear as a dark spot on the eye. However, if it begins in the ciliary body or choroid, symptoms may appear as vision problems, if at all. In these cases, the disease is usually detected during a routine examination. Chances of recovery and response to treatment depend on the location of the melanoma and whether it has spread. Posterior uveal tract melanomas (those cancers arising from the ciliary body or the choroid—the deeper parts of the eye) are typically more malignant, with a five-year mortality rate of 30% when the tumor has spread to areas outside of the eye. Anterior uveal tract melanomas (those arising from the iris) have a 2% to 3% mortality rate over five years. Thus, in one embodiment of the invention, intraocular melanoma is treated using the system of the invention.

Standard treatment for intraocular melanoma typically includes surgical removal of the eye, or enucleation. Because of this procedure's effect on a patient's appearance, possible diagnostic uncertainties and the potential for the cancer to spread, alternative treatments have been introduced. These treatments include radiation with radioactive plaques, laser photocoagulation, transpupillary thermotherapy and cryotherapy. Also contemplated is proton beam therapy which has the ability to precisely target eye tumors without causing any serious damage to healthy tissue surrounding the eye.

Choroidal metastasis occurs when cancer spreads to the choroidal layer of the eye from another primary site, like the breast. In these situations, the goal of treatment is to improve the patient's quality of life by preserving vision and preventing removal of the eye. Chemotherapy, external beam radiation therapy and proton therapy in combination with the system described above are contemplated by the present invention for the treatment of choroidal metastasis such that the therapeutic treatment allows for retention of the eye, achieves a high probability of local control, and helps avoid vision loss and pain.

Retinoblastoma is an uncommon childhood cancer. It begins in the retina, and accounts for about 3% of cancers in children younger than 15 years—about 4 cases per million. It most often occurs before the age of two, with 95% of retinoblastoma diagnosed before the age of five. The tumor may affect one eye (about 75% of cases), or both eyes (25% of cases). More than 90% of retinoblastoma that does not spread beyond the eye will be cured. Retinoblastoma is sometimes caused by an inherited gene mutation; when it occurs in both eyes, it is always the result of a gene mutation. Treatment of retinoblastoma in accordance with the present invention contemplates a multidisciplinary approach, and involves treating the cancer as well as retaining vision. If the tumor is especially large, or if there is little expectation of retaining normal vision, surgery may be considered. Other options include cryotherapy, photocoagulation, chemotherapy and radiation therapy. External beam radiation therapy with protons has been used in select cases to control tumors. Proton therapy in combination with the system of the invention is also contemplated by the present invention.

Choroidal hemangiomas are benign vascular tumors that are usually well contained, and may cause a decrease in visual abilities. Treatment of choroidal hemangiomas is meant to reduce fluid collection under the retina and decrease the size of the tumor. Standard treatment involves laser photocoagulation, which successfully reattaches the retina, but may not always completely destroy the tumor. In recent years, radioactive plaque treatment and proton beam radiation treatments have been used. Proton beam therapy shares the precise tumor targeting ability of radioactive plaques, and is therefore contemplated for use with the system of the present invention.

In addition to the cancer treatment methods described above, the invention also contemplates manipulating the eye so as to move critical structures away from the treatment axis to deliver therapeutic amounts of radiation to tumors outside, but near, the eye. Thus, in one embodiment of the invention, the system is used to position the eye for the treatment of extraocular conditions.

In one embodiment of the invention, the device described above is utilized in combination with other therapeutics for the eye. For example, one or more therapy treatments such as cryotherapy, photocoagulation, chemotherapy and radiation therapy can be utilized in combination with the system of the present invention to provide therapeutic treatment of the eye.

From the foregoing, it can be seen how various objects and features of the invention are met. While certain aspects and embodiments of the disclosure have been described, these have been presented by way of example only, and are not intended to limit the scope of the disclosure. The methods and systems described herein may be embodied in a variety of other forms without departing from the spirit thereof. All publications and patents cited herein are expressly incorporated herein by reference for the purpose of describing and disclosing systems and methodologies which might be used in connection with the invention.

It is claimed:

1. A system for performing an ocular irradiation procedure on a patient's eye, comprising
    (a) a head support for supporting the patient's head,
    (b) an eye-contact device attachable to the front portion of the patient's eye, to stabilize the position of the eye relative to the eye-contact device,
    (c) means for determining the position of the patient's eye, the eye being stabilized with respect to the contact device, and with the patient's head supported in the head support, in an external coordinate system,
    (d) a source of a collimated irradiation beam, and
    (e) a beam-positioning assembly for positioning the beam source in the external coordinate system such that the beam, when activated, is aimed along a selected path at a selected coordinate in the external coordinate system corresponding to a selected target region in the patient's eye;
    wherein said determining means includes a position detector for determining the position of the contact device, and thus the position of the patient's eye attached to the contact device, in the external coordinate system;
    wherein the system further includes an eye-positioning assembly for moving the eye-contact device to place the device at a selected position in the external coordinate system, and the position detector is operable to determine the position of the contact device in the external coordinate system, with such placed at said selected position;
    wherein the eye-positioning assembly is operable to adjust the angular position of the contact device with respect to the patient's head, and the position detector detects an angle of a beam emanating from the contact device;
    wherein the eye-contact device includes (i) a concave contact surface adapted to be placed against the front surface of a patient's eye, (ii) an outer surface, (iii) a port in fluid communication with the contact surface, by which a negative pressure can be applied between the eye and the contact surface, to stabilize the position of the eye with respect to the contact device, and (iv) a connector carried on the outer surface of the device, and the system further includes a biasing mechanism coupled to the connector of the contact device for pressing the eye-contact device against the eye with a force sufficient to the hold the contact device against the eye, when the eye is stabilized with respect to the device by application of a negative pressure between the eye and the device's contact surface;
    wherein the eye-positioning assembly includes an arm that is pivotally attached to the connector of the eye-contact device, and an arm control mechanism for controlling the movement of the arm in at least one direction in the external coordinate system, and the position detector is operable to determine the position of the contact device in the external coordinate system from the position of the eye-positioning assembly arm in the external coordinate system;

wherein said determining means includes a reference-beam light source operatively connected to the irradiation-beam source, for producing a reference light beam along a path coincident with the collimated irradiation beam produced by the irradiation beam source, and said beam-positioning assembly is operable to place the irradiation beam source at a position such that the collimated irradiation beam is aimed at the selected target region of patient's eye.

2. The system of claim 1, wherein the position detector includes a plurality of beam elements mounted on the contact device, for directing beams in accordance with the position and orientation of the beam elements, sensors for detecting the directions of the beams, and a processor for determining from the detected beam directions, the position and orientation of the contact device in the external coordinate system.

3. The system of claim 1, which further includes a vacuum source operable to apply a negative pressure of between about 20-50 mm Hg to the contact device contact surface.

4. The system of claim 1, for use in treating macular degeneration in a patient eye, wherein the beam source is a source of soft collimated x-rays, and the beam-positioning assembly is operable to position the beam source to direct a collimated x-ray beam at the macular region of the eye, along a path through an outer side region of the eye that makes an angle with an axis normal to the cornea of the eye, between about 5 and 45 degrees.

5. The system of claim 1, wherein the eye-contact device is a curved structure which is centered on a center axis extending through the contact device, substantially normal thereto, and said connector is disposed along the center axis of the contact device.

6. The system of claim 1, wherein the eye-contact device is a curved structure which is centered on a center axis extending through the contact device, substantially normal thereto, and said connector is disposed along an axis offset from the center axis.

7. The system of claim 1, wherein the connector is detachably coupled to the biasing mechanism, allowing the mechanism to break away from the eye-contact device when an above-threshold force is applied by or to the eye.

8. A system for performing an ocular irradiation procedure on a patient's eye, comprising
(a) a head support for supporting the patient's head,
(b) an eye-contact device attachable to the front portion of the patient's eye, to stabilize the position of the eye relative to the eye-contact device,
(c) means for determining the position of the patient's eye, with the eye being stabilized with respect to the contact device, and with the patient's head supported in the head support, in an external coordinate system,
(d) a source of a collimated irradiation beam, and
(e) a beam-positioning assembly for positioning the beam source in the external coordinate system such that the beam, when activated, is aimed along a selected path at a selected coordinate in the external coordinate system corresponding to a selected target region in the patient's eye;
(f) a position detector for determining the position of the contact device, and thus the position of the patient's eye attached to the contact device, in the external coordinate system
(g) an eye-positioning assembly operable to adjust the angular position of the contact device with respect to the patient's head, the position detector being operable to detect an angle of a beam emanating from the contact device;
wherein the eye-contact device includes (i) a concave contact surface adapted to be placed against the front surface of a patient's eye, (ii) an outer surface, (iii) a port in fluid communication with the contact surface, by which a negative pressure can be applied between the eye and the contact surface, to stabilize the position of the eye with respect to the contact device, and (iv) a connector carried on the outer surface of the device, and the system further includes a biasing mechanism coupled to the connector of the contact device for pressing the eye-contact device against the eye with a force sufficient to the hold the contact device against the eye, when the eye is stabilized with respect to the device by application of a negative pressure between the eye and the device's contact surface;
wherein the eye-positioning assembly includes an arm that is pivotally attached to the connector of the eye-contact device, and an arm control mechanism for controlling the movement of the arm in at least one direction in the external coordinate system, and the position detector is operable to determine the position of the contact device in the external coordinate system from the position of the eye-positioning assembly arm in the external coordinate system;
wherein said determining means includes a reference-beam light source operatively connected to the irradiation-beam source, for producing a reference light beam along a path coincident with the collimated irradiation beam produced by the irradiation beam source, and said beam-positioning assembly is operable to place the irradiation beam source at a position such that the collimated irradiation beam is aimed at the selected target region of patient's eye.

9. The system of claim 8, wherein the position detector includes a plurality of beam elements mounted on the contact device, for directing beams in accordance with the position and orientation of the beam elements, sensors for detecting the directions of the beams, and a processor for determining from the detected beam directions, the position and orientation of the contact device in the external coordinate system.

10. The system of claim 8, which further includes a vacuum source operable to apply a negative pressure of between about 20-50 mm Hg to the contact device contact surface.

11. The system of claim 8, for use in treating macular degeneration in a patient eye, wherein the beam source is a source of soft collimated x-rays, and the beam-positioning assembly is operable to position the beam source to direct a collimated x-ray beam at the macular region of the eye, along a path through an outer side region of the eye that makes an angle with an axis normal to the cornea of the eye, between about 5 and 45 degrees.

12. The system of claim 8, wherein the eye-contact device is a curved structure which is centered on a center axis extending through the contact device, substantially normal thereto, and said connector is disposed along the center axis of the contact device.

13. The system of claim 8, wherein the eye-contact device is a curved structure which is centered on a center axis extending through the contact device, substantially normal thereto, and said connector is disposed along an axis offset from the center axis.

14. The system of claim 8, wherein the connector is detachably coupled to the biasing mechanism, allowing the mechanism to break away from the eye-contact device when an above-threshold force is applied by or to the eye.

* * * * *